United States Patent
Fuchs et al.

(10) Patent No.: US 6,770,636 B2
(45) Date of Patent: Aug. 3, 2004

(54) PHENYL-AND PHENYLALKYL-SUBSTITUTED ETHANOLAMINES AND ETHYLENEDIAMINES

(75) Inventors: Klaus Fuchs, Gau-Algesheim (DE); Werner Stransky, Gau-Algesheim (DE); Matthias Grauert, Biberach (DE); Adrian Carter, Bingen (DE); Wolfram Gaida, Ingelheim (DE); Thomas Weiser, Nieder-Olm (DE); Helmut Ensinger, Ingelheim (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/912,163

(22) Filed: Jul. 24, 2001

(65) Prior Publication Data

US 2002/0042410 A1 Apr. 11, 2002

Related U.S. Application Data

(60) Provisional application No. 60/228,675, filed on Aug. 29, 2000.

(30) Foreign Application Priority Data

Aug. 18, 2000 (DE) .......................................... 100 40 901

(51) Int. Cl.[7] .......................... A61K 31/33; A61K 31/135
(52) U.S. Cl. ...................... 514/183; 514/649; 514/715; 514/644
(58) Field of Search ............................... 514/183, 649, 514/715, 644

(56) References Cited

FOREIGN PATENT DOCUMENTS

WO          9505363      *  2/1995

OTHER PUBLICATIONS

Chemical Abstract DN 100:174724.*
Chemical Abstract DN 113:4007.*
Nefzi et al, Tetrahedron 55/2,335–344(1999).*
Muller et al(PubMed Abstract 11099718, also cited as Neurolo.Sci. 81 81/1–2,98–103(2000).*
Gennari et al, Chemical Abstract DN 113:40077, also cited as Tetrahedron Letters, 30/38,5163–6(1989).*
Weinhardt et al, Chemical Abstract DN 100:174724, also cited as J. Medicinal Chemistry,27/5,616–27(1984).*
Nefzi et al, Chemical Abstract DN 130:196468, also cited as Tetrahedron, 55/2,335–344(1999).*
Bush Al(PubMed Abstract 12689772, also cited as Trends Neurosci. 26/4,207–14(2003).*
Markstein R (PubMed Abstract 2575520, also cited as Eur.eurol. 29/3, 33–41(1989).*
Farber et al(PubMed Abstract 9932393, also cited as Prog. Brain res. 116,421–37(1998).*

* cited by examiner

Primary Examiner—Richard Raymond
Assistant Examiner—Sudhaker B. Patel
(74) Attorney, Agent, or Firm—Robert P. Raymond; Timothy X. Witkowski; Anthony P. Bottino

(57) ABSTRACT

Compounds of formula 1,

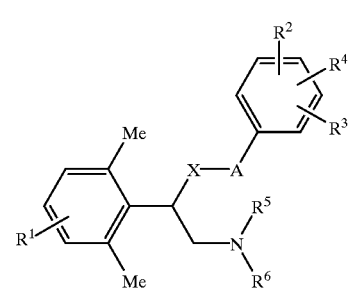

wherein:

$R^1$ is hydrogen, hydroxy, $CF_3$, $NO_2$, CN, halogen, $C_1$–$C_8$-alkyl, or $C_1$–$C_8$-alkoxy;

$R^2$, $R^3$, and $R^4$ independently of one another are hydrogen, $C_1$–$C_8$-alkyl, hydroxy, $NO_2$, CN, $C_1$–$C_8$-alkoxyl, $CF_3$, or halogen;

$R^5$ and $R^6$ independently of one another are hydrogen or a group consisting of $C_1$–$C_8$-alkyl, $C_2$–$C_8$-alkenyl, $C_3$–$C_8$-alkynyl, $C_3$–$C_8$-cycloalkyl, $C_3$–$C_8$-cycloalkyl-$C_1$–$C_6$-alkylene, $C_5$–$C_8$-cycloalkenyl, $C_5$–$C_8$-cycloalkenyl-$C_1$–$C_6$-alkylene, $C_6$–$C_{10}$-aryl, and $C_6$–$C_{10}$-aryl-$C_1$–$C_6$-alkylene, each optionally substituted by a group consisting of $C_1$–$C_6$-alkyl, $C_2$–$C_6$-alkenyl, halogen, $C_1$–$C_6$-alkyloxy, —$NH_2$, —NH($C_1$–$C_4$-alkyl), —N($C_1$–$C_4$-alkyl)$_2$, hydroxy, =O, —COOH, —CO—O$C_1$–$C_4$-alkyl, —$CONH_2$, —CONH($C_1$–$C_4$-alkyl), —CON($C_1$–$C_4$-alkyl)$_2$, and $CF_3$, or $R^5$ and $R^6$ together with the nitrogen atom are a saturated or unsaturated 5-, 6-, 7-, or 8-membered heterocyclic group optionally containing one or two further heteroatoms consisting of sulfur, oxygen, and nitrogen, and optionally mono-, di-, or trisubstituted by a group consisting of $C_1$–$C_4$-alkyl, hydroxy, =O, —COOH, —CO—O$C_1$–$C_4$-alkyl, —$CONH_2$, —CONH($C_1$–$C_4$-alkyl), —CON($C_1$–$C_4$-alkyl)$_2$, halogen, and benzyl;

X is oxygen, —NH—, —N(CHO)—, —N(CO—$C_1$–$C_6$-alkyl), —N($C_1$–$C_6$-alkyl), or —N($C_3$–$C_6$-cycloalkyl-$C_1$–$C_4$-alkylene); and A is a group consisting of $C_1$–$C_6$-alkylene, $C_2$–$C_6$-alkenylene, and $C_3$–$C_6$-alkynylene, each optionally substituted by a group consisting of halogen, =O, and hydroxy, or an optical isomer, enantiomer, tautomer, free base, or pharmacologically acceptable acid addition salt thereof; methods of making such compounds; pharmaceutical compositions thereof, and their use in treating or preventing certain diseases.

29 Claims, No Drawings

PHENYL- AND PHENYLALKYL- SUBSTITUTED ETHANOLAMINES AND ETHYLENEDIAMINES

The present patent application relates to new compounds of general formula 1

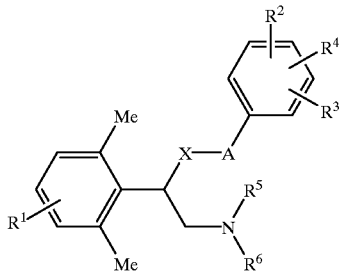

1 wherein the groups A, X, $R^1$, $R^2$, $R^3$, $R^4$, $R^5$, and $R^6$ have the meanings given in the specification and claims, processes for preparing them, and their use as pharmaceutical compositions, particularly as pharmaceutical compositions for the prevention or treatment of diseases the cause of which is based on a functional disorder caused by overstimulation.

BACKGROUND OF THE INVENTION

The aim of the present invention is to prepare new compounds which can be used as blockers of the voltage-dependent sodium channel. Compounds of this kind can be used to treat diseases which are caused by a functional disorder resulting from overstimulation. These include diseases such as arrhythmias, spasms, cardiac and cerebral ischemias, pain, and neurodegenerative diseases of various origins. These include, for example: epilepsy, hypoglycemia, hypoxia, anoxia, brain trauma, brain edema, cerebral stroke, perinatal asphyxia, degeneration of the cerebellum, amyotrophic lateral sclerosis, Huntington's disease, Alzheimer's disease, Parkinson's disease, cyclophrenia, hypotonia, cardiac infarction, heart rhythm disorders, angina pectoris, chronic pain, neuropathic pain, and local anesthesia.

DETAILED DESCRIPTION OF THE INVENTION

The problem stated above is solved by the compounds of general formula 1 disclosed in the description which follows.

The present patent application relates to new compounds of general formula 1

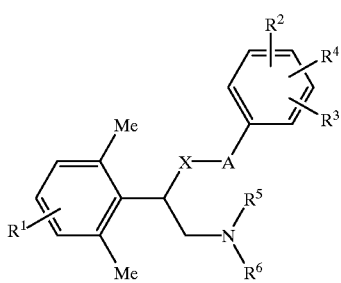

1 wherein:

$R^1$ denotes hydrogen, hydroxy, $CF_3$, $NO_2$, CN, halogen, $C_1$–$C_8$-alkyl, or $C_1$–$C_8$-alkoxy;

$R^2$, $R^3$, and $R^4$ independently of one another denote hydrogen, $C_1$–$C_8$-alkyl, hydroxy, $NO_2$, CN, $C_1$–$C_8$-alkyloxy, $CF_3$, or halogen;

$R^5$ and $R^6$ independently of one another denote hydrogen or a group selected from among $C_1$–$C_8$-alkyl, $C_2$–$C_8$-alkenyl, $C_3$–$C_8$-alkynyl, $C_3$–$C_8$-cycloalkyl, $C_3$–$C_8$-cycloalkyl-$C_1$–$C_6$-alkylene, $C_5$–$C_8$-cycloalkenyl, $C_5$–$C_8$-cycloalkenyl-$C_1$–$C_6$-alkylene, $C_6$–$C_{10}$-aryl, and $C_6$–$C_{10}$-aryl-$C_1$–$C_6$-alkylene, which may optionally be substituted by a group selected from among $C_1$–$C_6$-alkyl, $C_2$–$C_6$-alkenyl, halogen, $C_1$–$C_6$-alkyloxy, —$NH_2$, —NH($C_1$–$C_4$-alkyl), —N($C_1$–$C_4$-alkyl)$_2$, hydroxy, =O, —COOH, —CO—O$C_1$–$C_4$-alkyl, —$CONH_2$, —CONH($C_1$–$C_4$-alkyl), —CON($C_1$–$C_4$-alkyl)$_2$, and $CF_3$, or $R^5$ and $R^6$ together with the nitrogen atom denote a saturated or unsaturated 5-, 6-, 7-, or 8-membered heterocyclic group which optionally contains one or two further heteroatoms selected from sulfur, oxygen, and nitrogen and may optionally be mono-, di-, or trisubstituted by a group selected from $C_1$–$C_4$-alkyl, hydroxy, =O, —COOH, —CO—O$C_1$–$C_4$-alkyl, —$CONH_2$, —CONH($C_1$–$C_4$-alkyl), —CON($C_1$–$C_4$-alkyl)$_2$, halogen, and benzyl;

X denotes oxygen, —NH—, —N(CHO)—, —N(CO—$C_1$–$C_6$-alkyl), —N($C_1$–$C_6$-alkyl), or —N($C_3$–$C_6$-cycloalkyl-$C_1$–$C_4$-alkylene), preferably oxygen or —NH—;

A denotes a group selected from $C_1$–$C_6$-alkylene, $C_2$–$C_6$-alkenylene, and $C_3$–$C_6$-alkynylene, which may optionally be substituted by a group selected from halogen, =O, and hydroxy.

Preferred compounds of general formula 1 are those wherein $R^1$ denotes hydrogen, halogen, $C_1$–$C_6$-alkyl, $CF_3$, or methoxy;

$R^2$, $R^3$, and $R^4$ independently of one another denote hydrogen, $C_1$–$C_6$-alkyl, $C_1$–$C_6$-alkyloxy, $CF_3$, or halogen;

$R^5$ and $R^6$ independently of one another denote hydrogen or a group selected from among $C_1$–$C_6$-alkyl, $C_2$–$C_6$-alkenyl, $C_3$–$C_6$-alkynyl, $C_3$–$C_6$-cycloalkyl, $C_3$–$C_6$-cycloalkyl-$C_1$–$C_6$-alkylene, $C_5$–$C_6$-cycloalkenyl, $C_5$–$C_6$-cycloalkenyl-$C_1$–$C_6$-alkylene, phenyl, and phenyl-$C_1$–$C_6$-alkylene, which may optionally be substituted by a group selected from among $C_1$–$C_4$-alkyl, $C_2$–$C_4$-alkenyl, halogen, $C_1$–$C_4$-alkyloxy, hydroxy, —$CONH_2$, =O, and $CF_3$, or $R^5$ and $R^6$ together with the nitrogen atom denote a saturated or unsaturated 5-, 6-, or 7-membered heterocyclic group which optionally contains one or two further heteroatoms selected from sulfur, oxygen, and nitrogen and may optionally be mono-, di-, or trisubstituted by $C_1$–$C_4$-alkyl, —$CONH_2$, or hydroxy;

X denotes oxygen, —NH—, —N(CHO)—, —N(CO—$C_1$–$C_5$-alkyl), —N($C_1$–$C_5$-alkyl), or —N($C_3$–$C_6$-cycloalkyl-$C_1$–$C_4$-alkylene), preferably oxygen or —NH—; and A denotes $C_1$–$C_5$-alkylene, $C_2$–$C_4$-alkenylene, or $C_3$–$C_4$-alkynylene, preferably $C_1$–$C_5$-alkylene.

Particularly preferred are compounds of general formula 1, wherein $R^1$ denotes hydrogen, $C_1$–$C_4$-alkyl, or $CF_3$;

$R^2$, $R^3$, and $R^4$ independently of one another denote hydrogen, $C_1$–$C_4$-alkyl, $CF_3$, or halogen;

$R^5$ and $R^6$ independently of one another denote hydrogen, $C_1$–$C_6$-alkyl, $CF_3$—$C_1$–$C_6$-alkylene, preferably selected from —$CH_2$—$CF_3$, —$CH_2$—$CH_2$—$CF_3$, $C_2$–$C_6$-alkenyl, $C_3$–$C_6$-alkynyl, $C_3$–$C_6$-cycloalkyl, $C_3$–$C_6$-cycloalkyl-$C_1$–$C_6$-alkylene, preferably cyclopropylmethyl or cyclohexenemethyl, cyclohexenyl, cyclohexenyl-$C_1$–$C_6$-alkylene, propenyl-cyclohexenylene-$C_1$–$C_6$-alkylene, phenyl, or phenyl-$C_1$–$C_6$-alkylene, or $R^5$ and $R^6$ together with the nitrogen atom denote a saturated or unsaturated 5-, 6-, or 7-membered heterocyclic group, which optionally contains another nitrogen atom and may optionally be mono-, di-, or trisubstituted by $C_1$–$C_4$-alkyl, —$CONH_2$, or hydroxy;

X denotes oxygen, —NH—, —N(CHO)—, —N(CO-methyl), —N(CO-ethyl), —N($C_1$–$C_5$-alkyl), or —N($C_3$–$C_6$-cycloalkyl-methylene), preferably oxygen or —NH—; and A denotes —$CH_2$—, —$CH_2$—$CH_2$—, or —$CH_2$—$CH_2$—$CH_2$—.

Also particularly preferred are compounds of general formula 1, wherein:

$R^1$ denotes hydrogen or methyl;

$R^2$ and $R^3$ independently of one another denote hydrogen, methyl, fluorine, chlorine, or bromine;

$R^4$ denotes hydrogen, fluorine, chlorine, or bromine;

$R^5$ and $R^6$ independently of one another denote hydrogen, $C_1$–$C_6$-alkyl, $CF_3$–$C_1$–$C_6$-alkylene, preferably —$CH_2$—$CH_2$—$CF_3$, $C_2$–$C_6$-alkenyl, butenyl, pentenyl, $C_3$–$C_6$-cycloalkyl, preferably cyclohexyl, $C_3$–$C_6$-cycloalkyl-$C_1$–$C_6$-alkylene, cyclopropylmethyl, or cyclohexenemethyl, cyclohexenyl, cyclohexenyl-$C_1$–$C_6$-alkylene, preferably cyclohexenyl-$CH_2$—, or $R^5$ and $R^6$ together with the nitrogen atom denote a heterocyclic group selected from among pyrrolidine, piperidine, 1,2,3,6-tetrahydropyridine, and azepan;

X denotes oxygen, —NH—, —N(CHO)—, —N(CO-methyl), —N(CO-ethyl), —N(methyl)-, —N(ethyl)-, —N(propyl)-, —N(butyl)-, —N(pentyl)-, or —N(cyclopropylmethylene)-, preferably oxygen or —NH—; and A denotes —$CH_2$—, —$CH_2$—$CH_2$—, or —$CH_2$—$CH_2$—$CH_2$—.

Of particular importance according to the invention are compounds of general formula 1, wherein $R^1$ denotes hydrogen or methyl;

$R^2$ and $R^3$ independently of one another denote hydrogen, methyl, fluorine, chlorine, or bromine;

$R^4$ denotes hydrogen, fluorine, chlorine, or bromine;

$R^5$ and $R^6$ independently of one another denote hydrogen, methyl, propyl, butyl, hexyl, cyclopropylmethyl, or cyclohexenemethyl, or $R^5$ and $R^6$ together with the nitrogen atom denote a heterocyclic group selected from among pyrrolidine, piperidine, 1,2,3,6-tetrahydropyridine, and azepan;

X denotes oxygen, —NH—, —N(CHO)—, —N(CO-methyl), —N(CO-ethyl), —N(ethyl)-, —N(propyl)-, —N(butyl)-, —N(pentyl)-, or —N(cyclopropylmethylene)-, preferably oxygen or —NH—; and A denotes —$CH_2$—, —$CH_2$—$CH_2$—, or —$CH_2$—$CH_2$—$CH_2$—.

Of outstanding importance according to the invention are compounds of general formula 1, wherein $R^1$ denotes hydrogen or methyl;

$R^2$ and $R^3$ independently of one another denote hydrogen or fluorine;

$R^4$ denotes hydrogen;

$R^5$ and $R^6$ independently of one another denote hydrogen, butyl, hexyl, or cyclohexenemethyl, or $R^5$ and $R^6$ together with the nitrogen atom denote piperidine and 1,2,3,6-tetrahydropyridine;

X denotes oxygen or —NH—; and

A denotes —$CH_2$—$CH_2$— or —$CH_2$—$CH_2$—$CH_2$—.

Compounds of general formula 1, wherein $R^1$ denotes hydrogen, $R^2$ and $R^3$ are in the ortho position, and X, A, $R^2$, $R^3$, $R^4$, $R^5$, and $R^6$ may have the meanings given hereinbefore, correspond to general formula 1'.

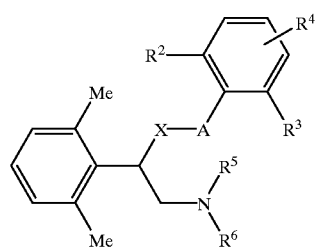

1'

These compounds are particularly important according to the invention.

Compounds of general formula 1, wherein $R^1$ denotes methyl and is in the para position, $R^2$ and $R^3$ are in the ortho position, and X, A, $R^2$, $R^3$, $R^4$, $R^5$, and $R^6$ may have the meanings given hereinbefore, correspond to general formula 1".

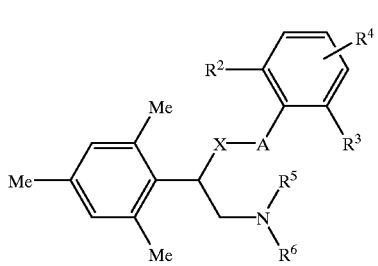

1"

These compounds are particularly important according to the invention. Of special importance are the compounds of general formulae 1, 1', and 1", wherein $R^4$ denotes hydrogen.

The invention relates to the compounds of formula 1 in question, optionally in the form of the individual optical isomers, mixtures of the individual enantiomers or racemates and in the form of the free bases or the corresponding acid addition salts thereof with pharmacologically acceptable acids, such as, for example, acid addition salts with hydrohalic acids, e.g., hydrochloric or hydrobromic acid, or organic acids, such as, e.g., oxalic, fumaric, or diglycolic acid, or methanesulfonic acid.

The present invention also relates to quaternary ammonium compounds such as may be formed from the compounds of formula 1 with alkyl halides of formula $R^7$—X.

Accordingly, the quaternary ammonium compounds of formula 1-Y are also important according to the invention:

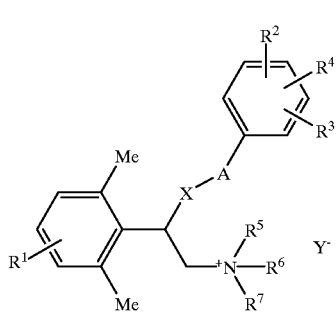

1-Y wherein the groups A, X, $R^1$, $R^2$, $R^3$, and $R^4$ may have the meanings given hereinbefore, $R^5$ and $R^6$ may have the meanings given hereinbefore with the exception of hydrogen, $R^7$ denotes $C_{1-4}$-alkyl, preferably methyl or ethyl, and Y denotes a halide selected from among chlorine, bromine, and iodine.

Compounds of general formula 1-Y, wherein $R^1$ denotes hydrogen, $R^2$ and $R^3$ are in the ortho position, and X, A, $R^2$, $R^3$, $R^4$, $R^5$, $R^6$, and $R^7$ may have the meanings given hereinbefore, correspond to general formula 1'-Y.

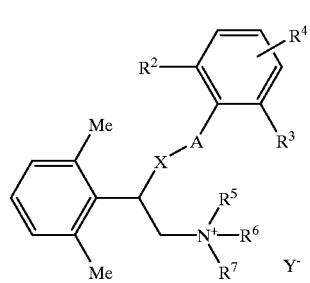

1'-Y

These compounds are particularly important according to the invention.

Compounds of general formula 1-Y, wherein $R^1$ denotes methyl and is in the para position, $R^2$ and $R^3$ are in the ortho position, and X, A, $R^2$, $R^3$, $R^4$, $R^5$, and $R^6$ may have the meanings given hereinbefore, correspond to general formula 1"-Y.

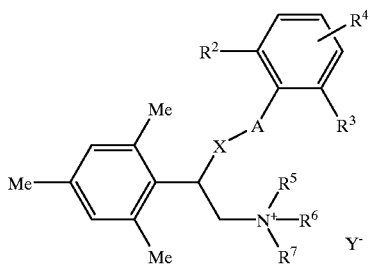

1"-Y

These compounds are also important according to the invention. Of special importance are the compounds of general formulae 1-Y, 1'-Y, and 1"-Y, wherein $R^4$ denotes hydrogen.

Of particular interest according to the invention are the following compounds:

(a) N-[2-[3-(2,6-difluorophenyl)propoxy]-2-(2,6-dimethylphenyl)ethyl]-N-n-butylamine;

(b) N-[[2-[3-(2,6-difluorophenyl)propoxy]-2-(2,6-dimethylphenyl)ethyl]-N-(2-ethylbutyl)-N,N-dimethylammonium iodide;

(c) 1-[2-[3-(2,6-difluorophenyl)propoxy]-2-(2,6-dimethylphenyl)ethyl]pyrrolidine;

(d) N-[2-[3-(2,6-difluorophenyl)propoxy]-2-(2,6-dimethylphenyl)ethyl]-N-(4-penten-1-yl)amine;

(e) N-[2-[3-(2,6-difluorophenyl)propoxy]-2-(2,6-dimethylphenyl)ethyl]-N-n-propylamine;

(f) N-[2-[3-(2,6-difluorophenyl)propoxy]-2-(2,4,6-trimethylphenyl)ethyl]-N,N-dimethylamine;

(g) 1-[2-[3-(2,6-difluorophenyl)propoxy]-2-(2,6-dimethylphenyl)ethyl]piperidine;

(h) N-[2-[3-(2,6-difluorophenyl)propoxy]-2-(2,6-dimethylphenyl)ethyl]-N-n-butyl-N,N-dimethylammonium iodide; and (i) N-[2-[3-(2,6-difluorophenyl)propoxy]-2-(2,6-dimethylphenyl)ethyl]-N-(1-cyclohexen-4-ylmethyl)-N,N-dimethylammonium iodide.

Unless otherwise stated, the general definitions are used as follows:

The term alkyl groups (including those which are part of other groups) denotes branched and unbranched alkyl groups with 1 to 8 carbon atoms, preferably 1 to 6 carbon atoms, most preferably 1 to 4 carbon atoms, which may optionally be substituted by one or more halogen atom(s), preferably fluorine. The following hydrocarbon groups are mentioned by way of example: methyl, ethyl, propyl, 1-methylethyl (isopropyl), n-butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl. Unless otherwise stated, lower alkyl groups having 1 to 4 carbon atoms such as methyl, ethyl, n-propyl, isopropyl, n-butyl, 1-methylpropyl, 2-methylpropyl, or 1,1-dimethylethyl are preferred. The definitions propyl, butyl, pentyl, etc., always include the associated isomeric groups. In some cases the common abbreviations are used for the abovementioned alkyl groups, such as Me for methyl, Et for ethyl, Prop for propyl, But for butyl, etc.

The term alkylene groups denotes branched and unbranched alkylene bridges with 1 to 6 carbon atoms, preferably 1 to 4 carbon atoms. The following are mentioned, for example: methylene, ethylene, propylene, butylene, etc. Unless otherwise stated, the terms propylene, butylene, etc., used above also include all the possible isomeric forms. Accordingly, the term propylene includes the isomeric bridges n-propylene, methylethylene, and dimethylmethylene and the term butylene includes the isomeric bridges n-butylene, 1-methylpropylene, 2-methylpropylene, 1,1-dimethylethylene, and 1,2-dimethylethylene.

Cycloalkyl generally denotes a saturated cyclic hydrocarbon group with 3 to 8 carbon atoms, which may optionally be substituted by a halogen atom or several halogen atoms, preferably fluorine, which may be identical to or different from one another. Cyclic hydrocarbons with 3 to 6 carbon atoms are preferred. Examples of these include cyclopropyl, cyclobutyl, cyclopentyl, cyclohexyl, cycloheptyl, and cyclooctyl.

Alkenyl generally denotes a branched or unbranched hydrocarbon group with 2 to 8 carbon atoms, preferably 2 to 6 carbon atoms, most preferably 2 to 4 carbon atoms, which may have one or more double bonds and may optionally be substituted by one or more halogen atoms, preferably fluorine, while the halogens may be identical to or different from one another. The following alkenyl groups are mentioned by way of example: vinyl, 2-propenyl (allyl), 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl 3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, and 1-ethyl-2-methyl-2-propenyl, etc.

Cycloalkenyl generally denotes a cyclic hydrocarbon group with 5 to 8 carbon atoms, which contains at least one double bond and may optionally be substituted by one halogen atom or several halogen atoms, preferably fluorine, which may be identical to or different from one another. Generally, cyclopentenyl or cyclohexenyl are preferred, and unless otherwise stated these groups may be substituted by $C_1$–$C_4$-alkyl or $C_2$–$C_4$-alkenyl.

Alkynyl generally denotes a branched or unbranched hydrocarbon group with 3 to 8 carbon atoms, preferably 3 to 6 carbon atoms, most preferably 3 to 5 carbon atoms, which may contain one or more triple bonds and may optionally be substituted by one or more halogen atoms, preferably fluorine, while the halogens may be identical to or different from one another. The following alkynyl groups are mentioned by way of example: ethynyl, 2-propynyl (propargyl), 2-butynyl, 3-butynyl, 1-methyl-2-propynyl, 2-methyl-2-propynyl, 2-pentynyl, 3-pentynyl, 4-pentynyl, 1-methyl-2-butynyl, 2-methyl-2-butynyl, 3-methyl-2-butynyl, 1-methyl-3-butynyl, 2-methyl-3-butynyl, 3-methyl-3-butynyl, 1,1-dimethyl-2-propynyl, 1,2-dimethyl-2-propynyl, 1-ethyl-2-propynyl, 2-hexynyl, 3-hexynyl, 4-hexynyl, 5-hexynyl, 1-methyl-2-pentynyl, 2-methyl-2-pentynyl, 3-methyl-2-pentynyl, 4-methyl-2-pentynyl, 1-methyl-3-pentynyl, 2-methyl-3-pentynyl, 3-methyl-3-pentynyl, 4-methyl-3-pentynyl, 1-methyl-4-pentynyl, 3-methyl-4-pentynyl, 4-methyl-4-pentynyl, 1,1-dimethyl-2-butynyl, 1,1-dimethyl-2-butynyl, 1,1-dimethyl-3-butynyl, 1,2-dimethyl-2-butynyl, 1,2-dimethyl-3-butynyl, 1,3-dimethyl-2-butynyl, 1,3-dimethyl-3-butynyl, 2,2-dimethyl-3-butynyl, 1-ethyl-2-butynyl, 1-ethyl-3-butynyl, 2-ethyl-1-butynyl, 2-ethyl-2-butynyl, 2-ethyl-3-butynyl, 1,1,2-trimethyl-2-propynyl, and 1-ethyl-1-methyl-2-propynyl.

Alkyloxy, which may also optionally be referred to as alkoxy, generally denotes a straight-chain or branched hydrocarbon group with 1 to 6 carbon atoms linked via an oxygen atom; a lower alkoxy group with 1 to 4 carbon atoms is preferred. The methoxy group is particularly preferred.

The term aryl denotes an aromatic ring system with 6 to 10 carbon atoms. Unless otherwise stated, the preferred aryl group is phenyl.

By cycloalkyl-alkylene is meant, for the purposes of the invention, cycloalkyl groups linked via an alkylene bridge.

By cycloalkenyl-alkylene is meant, for the purposes of the invention, cycloalkenyl groups linked via an alkylene bridge. By aryl-alkylene is meant, for the purposes of the invention, aryl groups linked via an alkylene bridge.

The following are mentioned as examples of N-linked 5-, 6-, 7-, or 8-membered, saturated or unsaturated heterocyclic groups which may be formed by the groups $R^5$ and $R^6$ together with the nitrogen atom: pyrrole, pyrroline, pyrrolidine, 1,2,3,6-tetrahydropyridine, piperidine, piperazine, morpholine, thiomorpholine, imidazole, imidazoline, imidazolidine, pyrazole, pyrazoline, pyrazolidine, azepan, azepine, diazepine, etc., preferably pyrrolidine, piperidine, 1,2,3,6-tetrahydropyridine, and azepan.

The compounds claimed are blockers of the voltage-dependent sodium channel. These are compounds which displace batrachotoxin (BTX) with a high affinity ($K_i$<1000 nM) competitively or non-competitively from the binding site on the sodium channel. Such substances exhibit "use-dependency" in the blocking of the sodium channels, i.e., in order to bind the substances at the sodium channel, the sodium channels first have to be activated. Maximum blockage of the sodium channels is only achieved after repeated stimulation of the sodium channels. Consequently, the substances bind preferentially to sodium channels which are activated a number of times. As a result, the substances are in a position to become effective particularly in those parts of the body which are pathologically overstimulated. The compounds of general formula 1 according to the invention can thus be used to treat diseases which are caused by a functional disorder resulting from overstimulation. These include diseases such as arrhythmias, spasms, cardiac and cerebral ischemias, pain, and neurodegenerative diseases of various origins. These include, for example: epilepsy, hypoglycemia, hypoxia, anoxia, brain trauma, brain edema, cerebral stroke, perinatal asphyxia, degeneration of the cerebellum, amyotrophic lateral sclerosis, Huntington's disease, Alzheimer's disease, Parkinson's disease, cyclophrenia, hypotonia, cardiac infarction, heart rhythm disorders, angina pectoris, chronic pain, neuropathic pain, and local anesthesia.

The blocking action on the sodium channel may be demonstrated by the test system which tests the BTX binding to the sodium channel [S. W. Postma & W. A. Catterall, Mol. Pharmacol 25, 219–227 (1984)] as well as by patch-clamp experiments which show that the compounds according to the invention block the electrically stimulated sodium channel in a "use-dependent" manner [W. A. Catterall, Trends Pharmacol. Sci., 8, 57–65 (1987)]. By a suitable choice of cell system (e.g., neuronal, cardiac, DRG cells) it is possible to test the effect of the substances on different subtypes of sodium channel.

The sodium channel blocking property of the compounds according to the invention can be demonstrated by the blocking of the veratridine-induced release of glutamate [S. Villanueva, P. Frenz, Y. Dragnic, and F. Orrego, Brain Res. 461, 377–380 (1988)]. Veratridine is a toxin which opens the sodium channel permanently. This leads to an increased influx of sodium ions into the cell. By means of the cascade described above, this sodium influx leads to an increased release of glutamate in the neuronal tissue. The compounds according to the invention antagonize this release of glutamate.

The anticonvulsant properties of the substances according to the invention were demonstrated by their protective effect against convulsions triggered by a maximum electric shock in mice [M. A. Rogawski & R. J. Porter, Pharmacol. Rev. 42, 223–286 (1990)].

Neuroprotective properties were demonstrated by a protective effect in a rat MCAO model [U. Pschorn & A. J. Carter, J. Stroke, Cerebrovascular Diseases, 6, 93–99 (1996)] and a malonate-induced lesion model [M. F. Beal, Annals of Neurology, 38, 357–366 (1995) and J. B. Schulz, R. T. Matthews, D. R. Henshaw, and M. F. Beal, Neuroscience, 71, 1043–1048 (1996)].

Analgesic effects can be investigated in models of diabetic neuropathy and in a ligature model [C. Courteix, M. Bardin, C. Chantelauze, J. Lavarenne, and A. Eschalier, Pain 57, 153–160 (1994); C. Courteix, A. Eschalier, and J. Lavarenne, Pain 53, 81–88 (1993); G. J. Bennett and Y.-K. Xie, Pain 33, 87–107 (1988)].

It has also been reported that sodium channel blockers can be used to treat cyclophrenia (manic depressive disorder) [J. R. Calabrese, C. Bowden, M. J. Woyshville; in: Psychopharmacology: The Fourth Generation of Progress (Eds.: D. E. Bloom and D. J. Kupfer) 1099–1111 (New York: Raven Press Ltd.)].

The claimed compounds 1 can be prepared using methods known from the prior art. Some methods of synthesis will now be described by way of example.

Starting from the benzaldehyde derivatives of formula 2 it is possible to obtain the compounds of general formula 6 (corresponding to compounds of formula 1 wherein X denotes O and the groups $R^5$ and $R^6$ denote hydrogen), using the procedure illustrated in Diagram 1.

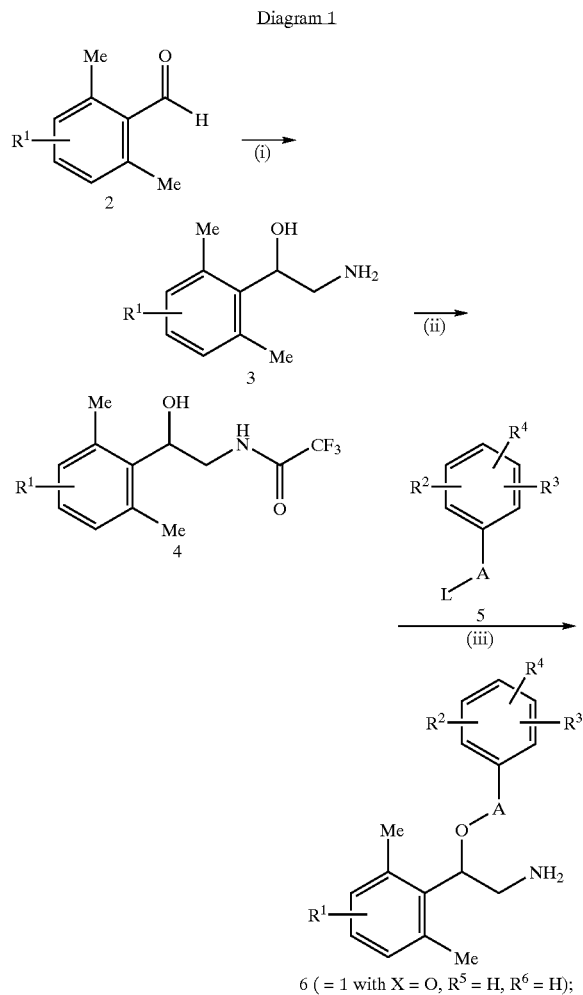

Diagram 1

Starting from the 2,6-dimethylbenzaldehyde derivatives 2 according to step (i) the 2-amino-ethanols 3 are obtained by first taking up 2 in trimethylsilylcyanide in the presence of a Lewis acid, preferably in the presence of zinc iodide. After the abovementioned reactants have been mixed together, preferably at ambient temperature, the mixture is diluted with an anhydrous organic solvent, preferably with an ethereal organic solvent, most preferably with diethylether, tetrahydrofuran, or dioxane. Then a reducing agent is added, preferably a metal hydride, most preferably a hydride selected from lithium aluminium hydride or sodium-bis(2-methoxyethoxy)aluminium hydride (Red-Al®). To complete the reaction, the mixture is stirred at elevated temperature, most preferably at the reflux temperature of the solvent used, for 0.5 to 4, preferably 2 hours. The reaction mixture is worked up in the usual way. The products are purified by crystallization or by chromatographic methods depending on their crystallization tendencies.

At the aminoalcohol stage 3 the racemate may optionally be separated into the enantiomers. The subsequent separation of the mixture of the enantiomeric aminoalcohols of type 3 thus obtained may be carried out using the methods of enantiomer separation known from the prior art, e.g., by reacting with malic acid, tartaric acid, mandelic acid, or camphorsulfonic acid, of which tartaric acid is particularly preferred.

The trifluoroacetates 4 (stage 3 (ii)) are prepared as follows from the compounds 3 optionally thus obtained in enantiomerically pure form. The alcohols 3 are dissolved in an organic solvent, preferably in an anhydrous organic solvent, most preferably in a solvent selected from among toluene, ether, dichloromethane, DMF, and ethyl acetate, and trifluoroacetic anhydride is added in the presence of an organic or inorganic base at ambient temperature or while cooling with ice, and the resulting mixture is stirred for 1 to 8 hours, preferably 2 to 6 hours, most preferably about 4 hours. The inorganic base used may be an alkali metal- or alkaline earth metal carbonate of lithium, sodium, potassium, or calcium, such as, sodium carbonate, lithium carbonate, potassium carbonate, calcium carbonate, and preferably potassium carbonate. The organic base is preferably an organic amine, most preferably diisopropylethylamine, triethylamine, a cyclic amine such as DBU, or pyridine. The abovementioned amines may optionally also be used as solvents. The reaction mixture is worked up in the usual way. The products are purified by crystallization or by chromatographic methods depending on their crystallization tendencies.

In order to prepare the compounds of formula 6 (corresponding to compounds of formula 1 wherein X denotes O and the groups $R^5$ and $R^6$ denote hydrogen) a compound 4 according to stage (iii) is dissolved in an organic solvent, preferably in an anhydrous organic solvent, most preferably in a solvent selected from among toluene, ether, dichloromethane, DMF, and ethyl acetate and combined with a compound of formula 5, optionally dissolved in one of the abovementioned organic solvents, in the presence of an organic base, preferably selected from diisopropyl ethylamine, triethylamine, cyclic amines such as DBU, and pyridine, at ambient temperature or in the presence of an inorganic base, preferably in the presence of alkali or alkaline earth metal carbonates of lithium, sodium, potassium, calcium such as sodium carbonate, lithium carbonate, potassium carbonate, calcium carbonate, or in the presence of the alkali metal hydrides or alkaline earth metal hydrides such as sodium hydride, calcium hydride, or potassium hydride, or in the presence of the alkali metal alkoxides, preferably potassium tert-butoxide, sodium methoxide, or sodium ethoxide, at ambient temperature or preferably at temperatures between −20° C. and ambient temperature, most preferably at about 0° C. When sodium hydride is used as the base, it may be helpful to use chelating agents such as crown ethers, preferably 15-crown-5. To complete the reaction the mixture is stirred at ambient temperature or at elevated temperature, preferably at the boiling temperature of the solvent used, for 2 to 24 hours, preferably 4 to 12 hours, most preferably 6 to 7 hours. The reaction mixture is worked up in the usual way. The products are purified by crystallization or by chromatographic methods depending on their crystallization tendencies.

An alternative method of obtaining compounds of general formula 6 (corresponding to 1 wherein X denotes oxygen and $R^5$ and $R^6$ denote hydrogen), starting from the benzaldehyde derivatives of formula 2, is the procedure illustrated in Diagram 2.

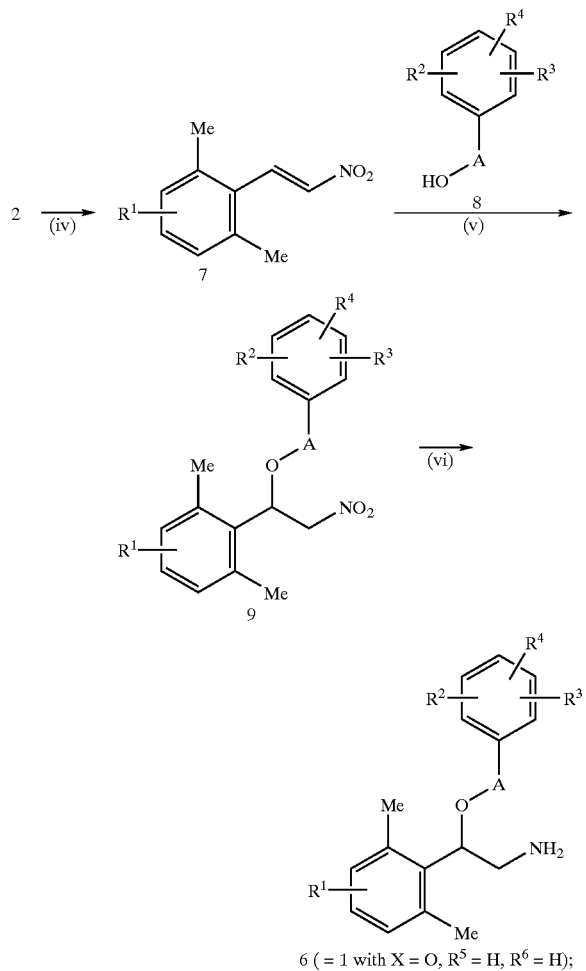

The ethers 9 may be obtained from the nitro compounds 7 by reacting with the alcohols 8. This is done as follows. The alcohol 8 is dissolved in an organic solvent, preferably in an anhydrous organic solvent selected from among methylene chloride, tetrahydrofuran, diethylether, and dioxane, and combined with a base selected from the alkali metal alkoxides such as sodium ethoxide, sodium methoxide, or potassium tert-butoxide, and the alkali metal- or alkaline earth metal hydrides, preferably sodium hydride. The mixture is stirred for 6 to 24, preferably about 10 to 14 hours at ambient temperature, optionally also at slightly elevated temperature and then a solution of the nitro compound 7, preferably in one of the abovementioned solvents, is added. Stirring is continued at a constant temperature until the reaction is complete. The reaction mixture is worked up in the usual way. The products are purified by crystallization or by chromatographic methods depending on their crystallization tendencies.

The final reduction of 9 leads to the compounds of formula 6 (corresponding to compounds of formula 1 wherein X denotes O and the groups $R^5$ and $R^6$ denote hydrogen). This reduction is preferably carried out by catalytic hydrogenation, preferably on palladium catalysts or on Raney nickel in alcoholic solvents, preferably in methanol, at ambient temperature. The reaction mixture is worked up in the usual way. The products are purified by crystallization or by chromatographic methods depending on their crystallization tendencies.

The ammonium salts 1-Y are synthesized in the same way as the preparation of compounds 1 starting from the amines 6, using standard methods (Diagram 3).

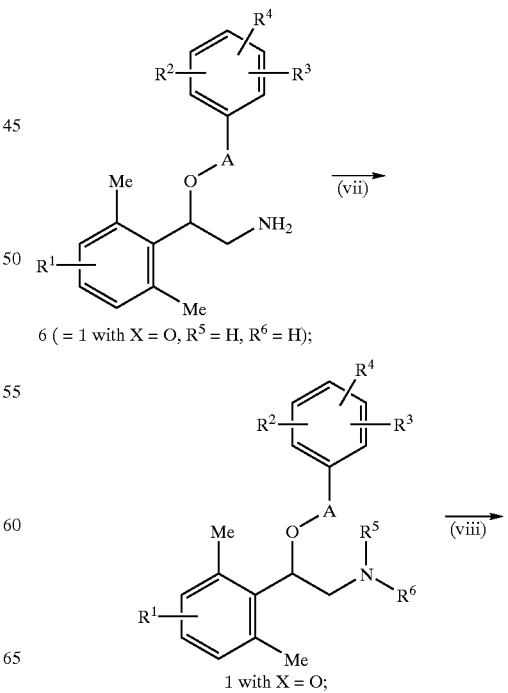

Diagram 2

Starting from the 2,6-dimethylbenzaldehyde derivatives (2) according to stage (iv) the reaction to obtain the α,β-unsaturated nitro compounds 7 is carried out using nitromethane in glacial acetic acid at elevated temperature, preferably at above 60° C., most preferably above 100° C., preferably at about 120° C. over a period of 2 to 8, preferably 3 to 6, most preferably about 4 hours. The reaction mixture is worked up in the usual way. The products are purified by crystallization or by chromatographic methods depending on their crystallization tendencies.

-continued

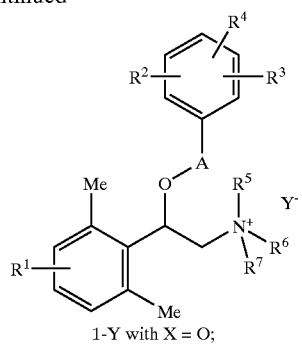

1-Y with X = O;

Diagram 3

The reaction according to stage (vii) may be carried out, on the one hand, in such a way that tertiary amines of formula 1 wherein neither $R^5$ nor $R^6$ denotes hydrogen, are obtained directly, or by a suitable choice of the reaction conditions may lead to secondary amines of formula 1 wherein either $R^5$ or $R^6$ denotes hydrogen. The latter may then be alkylated, on the one hand, by repeating stage (vii) to obtain tertiary amines, or may be subjected directly to stage (viii), in order to give access to the ammonium salts 1-Y.

In order to carry out the process according to stage (vii) an amine of general formula 6 is dissolved in an organic solvent such as dimethylformamide, dimethylacetamide, methylene chloride, or tetrahydrofuran, preferably dimethylformamide and most preferably anhydrous, optionally absolute dimethylformamide or methylene chloride. The solution thus obtained is combined with an inorganic or organic base and a corresponding alkylating agent. The base used may be an alkali metal- or alkaline earth metal carbonate of lithium, sodium, potassium, calcium such as sodium carbonate, lithium carbonate, potassium carbonate, or calcium carbonate, preferably potassium carbonate. It is also possible to use the hydrogen carbonates of lithium, sodium, and potassium. Moreover, the alkali metal- or alkaline earth metal hydroxides of lithium, sodium, potassium, magnesium, calcium, but preferably sodium hydroxide, potassium hydroxide, lithium hydroxide, and calcium hydroxide in alcohols or water may also be used. It is also possible to use, as further bases, alkoxides of alkali metals and alkaline earth metals, preferably the ethoxides of sodium and potassium. It is also possible to use alkali metal- and alkaline earth metal hydrides, preferably of potassium or sodium, preferably in inert solvents such as dimethylformamide, dimethylacetamide, methylene chloride, ethers, tetrahydrofuran, and toluene. The organic base is preferably an organic amine, most preferably diisopropylethylamine, triethylamine, a cyclic amine such as DBU, or pyridine. The alkylating agents used may be alkyl halides such as alkyl chloride, alkyl bromide, particularly alkyl iodide as well as alkyl tosylates, mesylates, triflates, and dialkylsulfates. The alkyl groups of the alkylating agents correspond to the definitions of $R^5$ and $R^6$ specified hereinbefore. The reaction mixture is stirred for 0.5 to 4 days, preferably 1 to 2 days at ambient temperature and evaporated to dryness. The reaction mixture is worked up in the usual way. The products are purified by crystallization or by chromatographic methods depending on their crystallization tendencies. The method described above for stage (vii) may be used to prepare the ammonium salts 1-Y starting from the amines 1 (stage viii).

Alternatively to the procedure described above the compounds of formula 1 may also be prepared according to stage (vii) by reductive amination of the amines 6 with carbonyl compounds in the presence of a reducing agent. The reaction of the amines 6 with the carbonyl compounds to obtain the Schiff bases formed as intermediates is carried out in solvents such as toluene, dichloromethane, ethyl acetate, ether, tetrahydrofuran etc., preferably at ambient temperature. It may be carried out in the presence of an acid, preferably in the presence of acetic acid. The subsequent reduction may be carried out with complex hydrides such as, for example, $LiAlH_4$, Li-alkoxyhydrides, $NaBH_4$, $NaBHCN_3$, $NaBH(OAc)_3$, etc. $NaBH_4$ is preferably used for the reaction with primary amines, $NaBH(OAc)_3$ for secondary amines. When preparing the methyl compounds by reacting with formalin it is advisable to use formic acid as solvent. The reaction mixture is worked up in the usual way. The products are purified by crystallization or by chromatographic methods depending on their crystallization tendencies.

Alternatively to the procedure described above the compounds of formula 1 may also be prepared by the procedure shown in Diagram 4.

Diagram 4

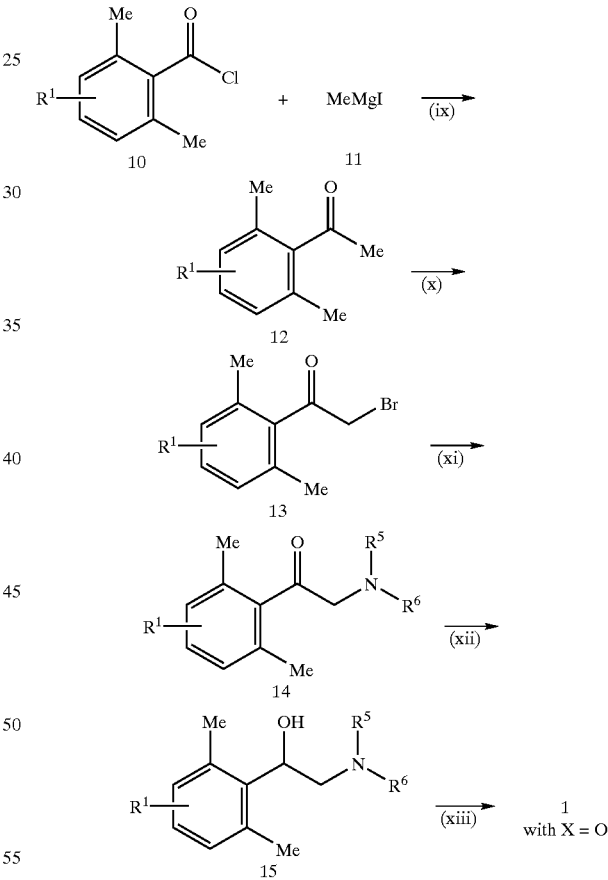

Diagram 4

Starting from suitably substituted benzoic acids the desired acetophenone intermediates 12 may be obtained by methods known from the literature (Recl. Trav. Chim. Pays-Bas 61, 539–544 (1942)) by Grignard reaction with the corresponding acid chlorides 10 (stage ix). These intermediates 12 are preferably brominated in ether to form the compounds 13 (stage x) and conveniently converted without further purification into the aminoethanol intermediates 15 via the aminoketones 14 and immediate reduction thereof (stage xii), preferably with sodium boranate in isopropanol or with lithium alanate in diethylether or tetrahydrofuran. Optically active aminoethanol intermediates 15 may be obtained stereospecifically by asymmetric hydrogenation using methods known from the literature e.g., with rhodium catalysts using (S,S)- or (R,R)-BCPM (Chem. Pharm. Bull. 43, 738 (1995)).

Etherification to obtain the compounds 1 (wherein X denotes oxygen) with variation of the chain length of A is carried out for example using benzylhalides, preferably using potassium tert-butoxide as auxiliary base (A=$C_1$), by Reppe reaction using optionally substituted phenylacetylenes and subsequent hydrogenation of the resulting Z/E olefins (A=$C_2$) and by Williamson etherification using phenylalkylhalides, preferably using crown ethers (e.g., A is $C_3$). At this point reference should also be made to the general remarks on stage (iii) according to Diagram 1 which are also applicable here.

Starting from the compounds of formula 3 the compounds of general formula 1 wherein X denotes —NH— may also be obtained by the method shown in Diagram 5.

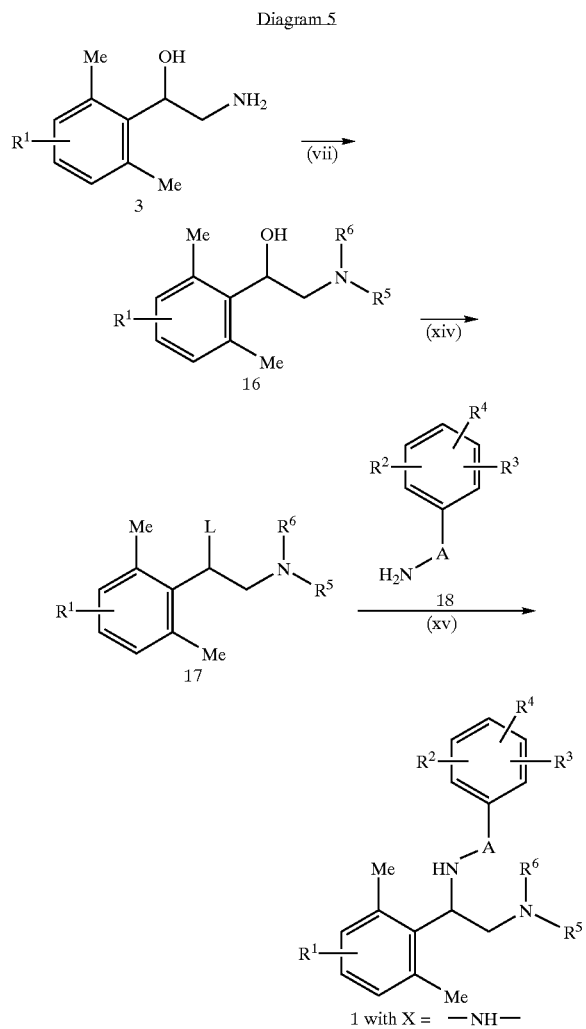

Diagram 5

To perform the process according to stage (vii) an amine of general formula 3 is dissolved in an organic solvent such as dimethylformamide, dimethylacetamide, methylene chloride, or tetrahydrofuran, preferably dimethylformamide, and most preferably anhydrous, optionally absolute dimethylformamide or methylene chloride. The solution thus obtained is combined with an inorganic or organic base and a corresponding alkylating agent. The base used may be an alkali metal carbonate or alkaline earth metal carbonate of lithium, sodium, potassium, calcium such as sodium carbonate, lithium carbonate, potassium carbonate, or calcium carbonate, preferably potassium carbonate. It is also possible to use the hydrogen carbonates of lithium, sodium, and potassium. Moreover, the alkali metal hydroxides or alkaline earth metal hydroxides of lithium, sodium, potassium, magnesium, calcium, but preferably sodium hydroxide, potassium hydroxide, lithium hydroxide, and calcium hydroxide in alcohols or water may also be used. It is also possible to use, as further bases, alkoxides of alkali metals and alkaline earth metals, preferably the ethoxides of sodium and potassium. It is also possible to use alkali metal hydrides or alkaline earth metal hydrides, preferably of potassium or sodium, preferably in inert solvents such as dimethylformamide, dimethylacetamide, methylene chloride, ethers, tetrahydrofuran, and toluene. The organic base is preferably an organic amine, most preferably diisopropylethylamine, triethylamine, a cyclic amine such as DBU, or pyridine. The alkylating agents used may be alkyl halides such as alkyl chloride, alkyl bromide, particularly alkyl iodide as well as alkyl tosylates, mesylates, triflates, and dialkylsulfates. The alkyl groups of the alkylating agents correspond to the definitions of $R^5$ and $R^6$ specified hereinbefore. The reaction mixture is stirred for 0.5 to 4 days, preferably 1 to 2 days at ambient temperature and evaporated to dryness. The reaction mixture is worked up in the usual way. The products 16 are purified by crystallization or by chromatographic methods depending on their crystallization tendencies.

The compounds of formula 17 wherein L denotes a leaving group, selected from chlorine, bromine, iodine, methanesulfonate, trifluoromethanesulfonate, or p-toluenesulfonate may be prepared from the compounds of formula 16 by reaction according to stage (xiv). If $R^5$ or $R^6$ equals hydrogen, protecting groups according to the prior art should be used. If L denotes chlorine or bromine, the reaction may be performed using common halogenation reagents. If L denotes methanesulfonate, trifluoromethanesulfonate, or p-toluenesulfonate the compounds 16 may be reacted with the corresponding sulfonic acid chlorides or anhydrides to obtain the compounds 17 in inert solvents such as dimethylformamide, dimethylacetamide, methylene chloride, ethers, tetrahydrofuran, and toluene in the presence of organic amines such as, preferably, diisopropylethylamine, triethylamine, cyclic amines such as DBU, or pyridine.

The compounds of formula 1 wherein X denotes —NH— may be obtained from the compounds 17 by reacting with the amines 18 under the reaction conditions described hereinbefore for stage (vii). The compounds of formula 1 wherein X denotes —N($C_1$–$C_6$-alkyl)- or —N($C_3$–$C_6$-cycloalkyl-$C_1$–$C_4$-alkylene)- may also be obtained therefrom. This reaction is carried out under the reaction conditions described for stage (vii) by alkylation of the compounds of formula 1 wherein X is —NH— with alkylating reagents $C_1$–$C_6$-alkyl-L or $C_3$–$C_6$-cycloalkyl-$C_1$–$C_4$-alkyl-L, where L may have the meanings given hereinbefore.

Starting from the compounds of formula 1 wherein X is —NH—, the compounds of general formula 1 wherein X denotes —N(CHO)— or —N(CO—$C_1$–$C_6$-alkyl)- may be obtained by the method illustrated in Diagram 6.

Diagram 6: Formylation or Acylation

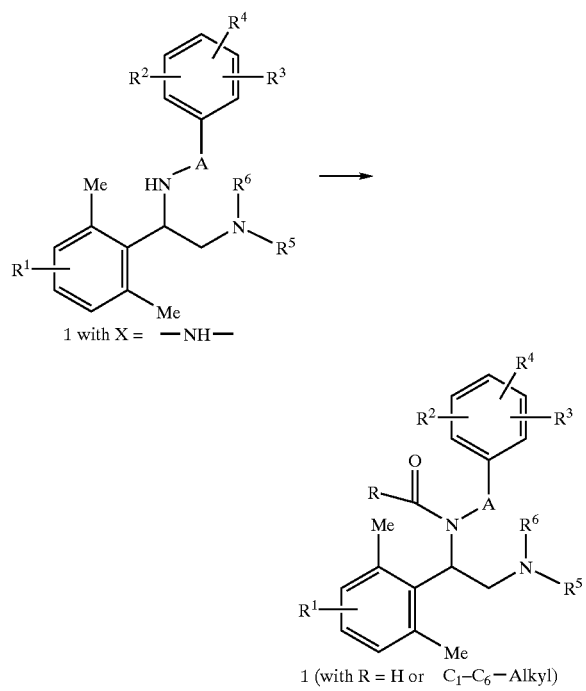

1 with X = —NH—

1 (with R = H or C$_1$-C$_6$—Alkyl)

Diagram 6

The reactions according to Diagram 6 may be carried out analogously to formulation and acylation processes which are known per se.

The Examples which follow serve only to illustrate the invention without restricting its subject matter.

EXAMPLE 1

2-[3-(2,6-difluorophenyl)propoxy]-2-(2,6-dimethylphenyl) ethylamine

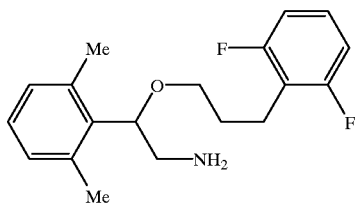

Synthesis of the Precursors 2, 5, and 8

1,1: 2,6-dimethylbenzaldehyde (corresponding to the compound of formula 2)

336 ml (0.54 mol) of a 1.6 M solution of n-butyllithium in hexane is added dropwise within 1 hour to a solution of 100 g (0.54 mol) of 2-bromo-1,3-dimethylbenzene in 690 ml of THF cooled to –65° C. The mixture is then stirred for 1 hour at the same temperature. Then 100 ml of DMF is added dropwise at –65° C. and the mixture is left to react for 30 minutes at this temperature. It is poured onto 500 ml of ice/135 ml of concentrated hydrochloric acid. The organic phase is separated off and the aqueous phase is extracted with ethyl acetate. The combined organic phases are dried and evaporated down. Yield: 85.0 g of light-yellow oil.

1.2: 3-(2,6-difluorophenyl)propan-1-ol (corresponding to the compound of formula 8) 1.2.1: diethyl 2-(2,6-difluorobenzyl)malonate 19.3 g (121 mmol) of diethyl malonate is placed in 700 ml of THF and 14.9 g (132 mmol) of potassium tert-butoxide is added. The mixture is stirred for 1 hour and 25 g (121 mmol) of 2,6-difluorobenzylbromide (3) is added. After 3 hours stirring at ambient temperature, the mixture is suction filtered through kieselguhr and concentrated by evaporation. Yield: 33.1 g of light-yellow oil.

1.2.2: monoethyl 2-(2,6-difluorobenzyl)malonate 33.1 g (116 mmol) of diethyl 2-(2,6-difluorobenzyl) malonate (Example 1.2.1) is dissolved in 120 ml of ethanol and, while cooling with ice 15 ml of a 40% sodium hydroxide solution is added. The mixture is stirred for 4 hours at ambient temperature, then the organic solvent is distilled off and the residue is washed with water. The aqueous solution is washed with dichloromethane and acidified with hydrochloric acid. It is extracted with dichloromethane, evaporated down, and a slowly crystallizing brown oil is obtained. Yield 21.5 g, melting point: 60° C.

1.2.3: ethyl 3-(2,6-difluorophenyl)propionate 21.5 g (83.3 mmol) of monoethyl 2-(2,6-difluorobenzyl) malonate (Example 1.2.2) is heated with stirring for 4 hour, without a solvent (bath temperature 160° C.). A light-brown liquid is obtained. Yield: 17.6 g.

1.2.4: 3-(2,6-difluorophenyl)propan-1-ol (corresponding to the compound of formula 8)

8.80 g (41.0 mmol) of ethyl 3-(2,6-difluorophenyl) propionate (Example 1.2.3) dissolved in 60 ml of THF is added dropwise while cooling with ice to a suspension of 1.71 g (41.1 mmol) of lithium aluminium hydride in 40 ml of THF. The mixture is stirred first for 1 hour at ambient temperature, then for 2 hours at 75° C. Diammonium tartrate solution and magnesium sulfate are added, the solution is separated off and the residue is washed with ethyl acetate. After drying and evaporation, a clear liquid is obtained. Yield: 5.67 g.

1.2.5: 2-(3-bromopropyl)-1,3-difluorobenzene (compound of formula 5)

6.86 g (39.8 mmol) of 3-(2,6-difluorophenyl)propan-1-ol (Example 1.2.4) is dissolved in 50 ml toluene and 19.1 g (92.0 mmol) of thionyl bromide is added. The mixture is refluxed for 3 hours, the solvent is eliminated and excess thionyl bromide is eliminated. Then the residue is purified by flash chromatography (cyclohexane). Yield: 6.98 g.

Alternative Method of Synthesis According to Diagram 1

1.3: 2-Amino-1-(2,6-dimethylphenyl)ethanol (corresponding to the compound of formula 3)

Method According to Stage (i)

15.7 ml (117 mmol) of trimethylsilylcyanide and 10.0 g (110 mmol) of zinc diiodide are added to 14.4 g (107 mmol) of 2,6-dimethylbenzaldehyde (Example 1.1). The mixture is stirred for 30 minutes at ambient temperature and 150 ml of ether is added. Then 8.10 g (213 mmol) of lithium aluminium hydride is added so that the mixture boils gently. After it has all been added, the mixture is stirred for 2 hours while refluxing. It is then carefully hydrolyzed with diammonium tartrate solution while cooling with ice. The mixture is suction filtered through magnesium sulfate and washed with ether. It is evaporated down and the product is obtained in the form of yellow crystals. Yield: 7.0 g, MS: m/z 166 [(M+H)$^+$].

1.4: N-[2-(2,6-dimethylphenyl)-2-hydroxyethyl] trifluoroacetamide (corresponding to the compound of formula 4)

Process According to Stage (ii)

2.00 g (12.1 mmol) of 2-amino-1-(2,6-dimethylphenyl) ethanol (Example 1.3) is dissolved in 100 ml dichloromethane, combined with 3.68 g (17.5 mmol) of trifluoroacetic anhydride and 1.60 g (15.8 mmol) of triethylamine and stirred for 4 hours in the ice bath. The mixture is evaporated down, the residue is taken up in 100 ml of dichloromethane and washed with 30 ml of saturated sodium hydrogen carbonate solution. The organic phase is dried and evaporated down and the crude product is purified by flash chromatography (dichloromethane/ethanol 90:10). Yield: 3.11 g, melting point: 96° C.

1.5: 2-[3-(2,6-difluorophenyl)propoxy]-2-(2,6-dimethylphenyl)ethylamine (corresponding to the compound of formula 6)

Process According to Stage (iii)

261 mg (1.00 mmol) of N-[2-(2,6-dimethylphenyl)-2-hydroxyethyl]trifluoroacetamide (Example 1.4) is dissolved in 3 ml of THF and, while cooling with ice, 70.0 mg (1.46 mmol) of sodium hydride (50% suspension in mineral oil) is added. After 5 minutes, 230 µL (1.13 mmol) of 15-crown-5 is added and stirring is continued for a further 5 minutes. 236 mg (1.00 mmol) of 2-(3-bromopropyl)-1,3-difluorobenzene is added (Example 1.2) and stirring is continued for 2 hours at ambient temperature. The mixture is then refluxed for 7 hours. The mixture is purified by flash chromatography (dichloromethane/ethanol 95:5). Yield: 120 mg, melting point: 166° C.

Alternative Method of Synthesis According to Diagram 2

1.6: 1,3-dimethyl-2-(2-nitrovinyl)benzene (corresponding to the compound of formula 7)

Process According to Stage (iv)

27.2 g of ammonium acetate and 48 ml (900 mmol) of nitromethane are added to 40.0 g (300 mmol) of 2,6-dimethylbenzaldehyde (Example 1.1) in 160 ml glacial acetic acid. The mixture is heated for 4 hours to 120° C. and poured onto 500 ml of ice. After thawing, it is extracted with ethyl acetate, the organic phase is washed with saturated sodium chloride solution, dried and evaporated down. The crude product is purified by flash chromatography (cyclohexane/ethyl acetate 80:20). Yield: 15.0 g of slowly crystallizing yellow oil.

1.7: 2-(1-(2,6-difluorophenylpropyloxy)-2-nitroethyl)-1,3-dimethylbenzene (corresponding to the compound of formula 9)

Process According to Stage (v)

1.20 g (25.0 mmol) of sodium hydride (50% suspension in mineral oil) is added to 4.30 g (24.3 mmol) of 3-(2,6-difluorophenyl)propan-1-ol (Example 1.2.4) dissolved in 20 ml of THF. The mixture is stirred for 14 hours at ambient temperature and then 4.30 g (24.1 mmol) of 1,3-dimethyl-2-(2-nitrovinyl)benzene (Example 1.6) dissolved in 40 ml of THF is added dropwise. It is stirred for 6 hours at ambient temperature, acidified with glacial acetic acid, diluted with water and extracted with ethyl acetate. The organic phase is washed with saturated sodium chloride solution, dried and evaporated down. The crude product is purified by flash chromatography (cyclohexane/ethyl acetate 90:10). Yield: 3.20 g.

1.8: 2-[3-(2,6-difluorophenyl)propoxy]-2-(2,6-dimethylphenyl)ethylamine (corresponding to the compound of formula 6)

Process According to Stage (vi)

1.50 g (4.29 mmol) of 2-(1-(2,6-difluorophenylpropyloxy)-2-nitroethyl)-1,3-dimethylbenzene (Example 1.7) dissolved in 30 ml methanol is hydrogenated for 6 hours at atmospheric pressure over 1.0 g of Raney nickel. The catalyst is separated off, the remainder is evaporated down and purified by flash chromatography (dichloromethane/ethanol 95:5). Yield: 745 mg, yellow oil.

EXAMPLE 2

N-[2-[3-(2,6-difluorophenyl)propoxy]-2-(2,6-dimethylphenyl)ethyl]-N,N-bis(2-ethylbutyl)amine

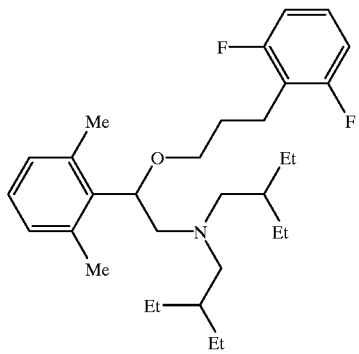

Process According to Stage (vii)

126 mg (0.39 mmol) of 2-[3-(2,6-difluorophenyl)propoxy]-2-(2,6-dimethylphenyl)ethylamine (Example 1) is placed in 4 ml of dichloromethane and combined with 24 mg (0.39 mmol) of glacial acetic acid and 39.5 mg (0.39 mmol) of 2-ethylbutyraldehyde. After 7 minutes, 117 mg (0.55 mmol) of sodium triacetoxyborohydride is added. The mixture us stirred for 2 hours at ambient temperature, then combined with 10% sodium hydrogen carbonate solution and stirred for a further 30 minutes at ambient temperature. The phases are separated, the organic phase is washed with saturated sodium chloride solution, dried, evaporated down, and the crude product is separated by flash chromatography (dichloromethane/ethanol 95:5), with [2-[3-(2,6-difluorophenyl)propoxy]-2-(2,6-dimethylphenyl)ethyl]-bis(2-ethylbutyl)amine being eluted first. Yield: 72 mg, colorless oil, MS: m/z 488 [(M+H)$^+$].

EXAMPLE 3

N-[2-[3-(2,6-difluorophenyl)propoxy]-2-(2,6-dimethylphenyl)ethyl]-N-(2-ethylbutyl)amine

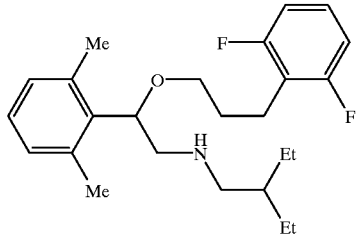

Prepared analogously to Example 2, the title compound being eluted second during the chromatographic separation. Yield: 61 mg, colorless oil, MS: m/z 404 [(M+H)$^+$].

EXAMPLE 4

N-[2-[3-(2,6-difluorophenyl)propoxy]-2-(2,6-dimethylphenyl)ethyl]-N-(2-ethylbutyl)-N-methylamine

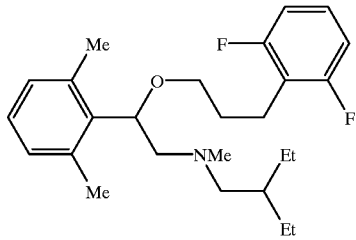

Process According to Stage (vii)

45 mg (0.11 mmol) of N-[2-[3-(2,6-difluorophenyl)propoxy]-2-(2,6-dimethylphenyl)ethyl]-N-(2-ethylbutyl)amine (Example 3) is dissolved in 2 ml of formic acid and combined with 1 ml of 37% formalin solution. The mixture is stirred for 4 hours at a bath temperature of 120° C., cooled, diluted with water and extracted with dichloromethane. The residue obtained after drying and evaporation is purified by flash chromatography (dichloromethane/ethanol 95:5). Yield: 15 mg, MS: m/z 418 [(M+H)$^+$].

EXAMPLE 5

N-[2-[3-(2,6-difluorophenyl)propoxy]-2-(2,6-dimethylphenyl)ethyl]-N-(2-ethylbutyl)-N,N-dimethylammonium iodide

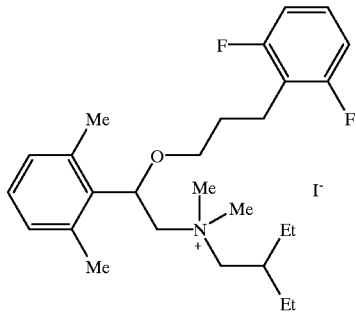

Process According to Stage (viii)

30.0 mg (74 μmol) N-[2-[3-(2,6-difluorophenyl)propoxy]-2-(2,6-dimethylphenyl)ethyl]-N-(2-ethylbutyl)amine (Example 3) is dissolved in 3 ml of acetonitrile and combined with 20.5 mg (148 μmol) of potassium carbonate, 6.0 mg (37 μM) of potassium iodide and 22.0 mg (155 μmol) of methyl iodide. The mixture is stirred for 3 hours at ambient temperature, the solvent is eliminated and the residue is purified by flash chromatography (dichloromethane/ethanol 95:5). Yield: 33 mg, MS: m/z 432 [(M+H)$^+$].

EXAMPLE 6

1-[2-[3-(2,6-difluorophenyl)propoxy]-2-(2,6-dimethylphenyl)ethyl]-pyrrolidine

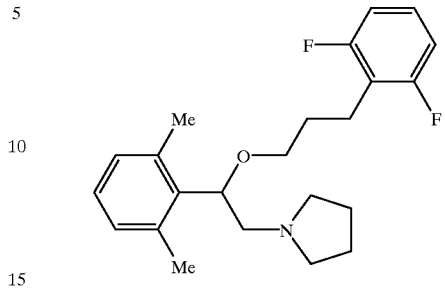

Process According to Stage (vii)

163 mg (0.51 mmol) of 2-[3-(2,6-difluorophenyl)propoxy]-2-(2,6-dimethylphenyl)ethylamine (Example 1), 110 mg (0.51 mmol) of 1,4-dibromobutane, 200 mg of potassium carbonate, and 50 mg of potassium iodide dissolved in 20 ml of acetonitrile is refluxed for 4 hours. The mixture is then evaporated down and the residue is purified by flash chromatography (dichloromethane/ethanol 95:5), in order to obtain the product as a white crystalline solid. Yield: 58 mg, melting point: 173° C.–175° C.

EXAMPLE 7

1-[2-[3-(2,6-difluorophenyl)propoxy]-2-(2,6-dimethylphenyl)ethyl]-1-methylpyrrolidinium iodide

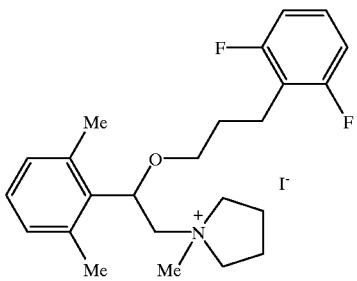

Process According to Stage (viii)

25.0 mg (70 μmol) of 1-[2-[3-(2,6-difluorophenyl)propoxy]-2-(2,6-dimethylphenyl)ethyl]pyrrolidine (Example 6), 10.0 mg (70 μmol) of methyl iodide, 20.0 mg potassium carbonate, and 6.0 mg potassium iodide are stirred in 2 ml of acetonitrile for 14 hours at ambient temperature. The mixture is evaporated down and the residue is purified by flash chromatography (dichloromethane/ethanol 95:5). Yield: 20.0 mg, MS: m/z 389 [(M+H)$^+$].

EXAMPLE 8

N-[2-[3-(2,6-difluorophenyl)propoxy]-2-(2,6-dimethylphenyl)ethyl]-N,N-dimethylamine

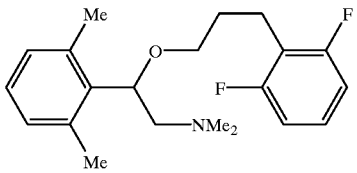

Process According to Stage (vii)

200 mg (0.63 mmol) of 2-[3-(2,6-difluorophenyl)propoxy]-2-(2,6-dimethylphenyl)ethylamine (Example 1) is dissolved in 12 ml of formic acid and combined with 6 ml of a 37% formalin solution. The mixture is stirred for 5 hours at 120° C., poured onto ice, and adjusted to pH 13–14 with concentrated sodium hydroxide solution. It is then extracted with ether, the organic phase is dried and evaporated down, as a result of which the product is obtained as a yellowish oil. Yield: 170 mg, MS: m/z 348 [(M+H)+].

EXAMPLE 9

N-[2-[3-(2,6-difluorophenyl)propoxy]-2-(2,6-dimethylphenyl)ethyl]-N-cyclopropylmethylamine

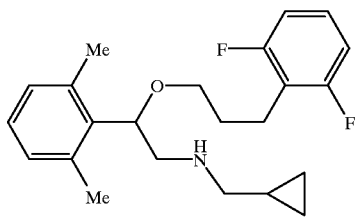

Prepared analogously to Example 3; oil; MS: m/z 374 [(M+H)+].

EXAMPLE 10

N-[2-[3-(2,6-difluorophenyl)propoxy]-2-(2,6-dimethylphenyl)ethyl]-N-cyclopropylmethyl-N-methylamine

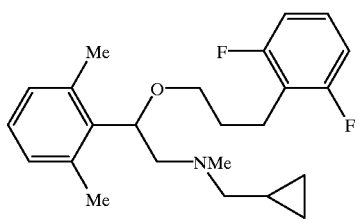

Prepared analogously to Example 4, starting from Example 9; melting point: 78° C.; MS: m/z 388 [(M+H)+].

EXAMPLE 11

N-[2-[3-(2,6-difluorophenyl)propoxy]-2-(2,6-dimethylphenyl)ethyl]-N,N-bis(1-cyclohexen-4-yl-methyl)amine

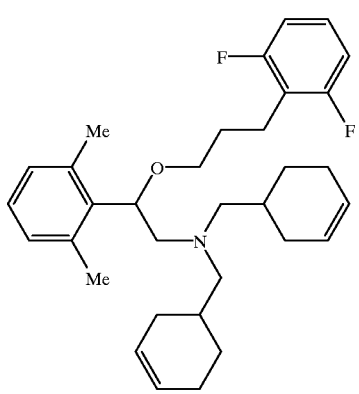

Prepared analogously to Example 2; oil; MS: m/z 508 [(M+H)+].

EXAMPLE 12

N-[2-[3-(2,6-difluorophenyl)propoxy]-2-(2,6-dimethylphenyl)ethyl]-N-(1-cyclohexen-4-yl-methyl)amine

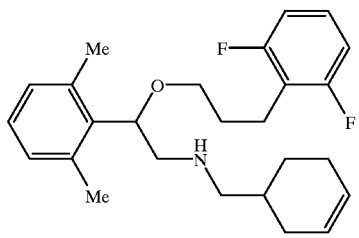

Prepared analogously to Example 3; oil; MS: m/z 414 [(M+H)+].

EXAMPLE 13

N-[2-[3-(2,6-difluorophenyl)propoxy]-2-(2,6-dimethylphenyl)ethyl]-N-n-butylamine

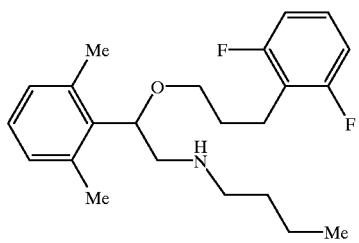

Prepared analogously to Example 3; oil ; MS: m/z 376 [(M+H)+].

EXAMPLE 14

1-[2-[3-(2,6-difluorophenyl)propoxy]-2-(2,6-dimethylphenyl)ethyl]piperidine

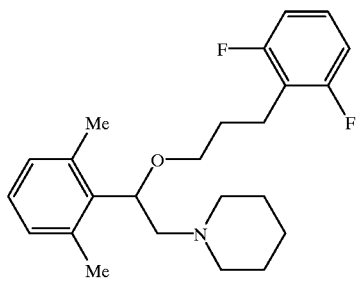

Prepared analogously to Example 6; melting point (hydrochloride): >200° C.; MS: m/z 388 [(M+H)+]. To prepare the hydrochloride of the title compound, the free base is taken up in a little ether and ethereal hydrochloric acid is added dropwise until the precipitation is complete. Then the solvent is removed, the residue is carefully washed with ether and dried.

EXAMPLE 15

N-[2-[3-(2,6-difluorophenyl)propoxy]-2-(2,6-dimethylphenyl)ethyl]-N-(1-cyclohexen-4-ylmethyl)-N,N-dimethylammonium iodide

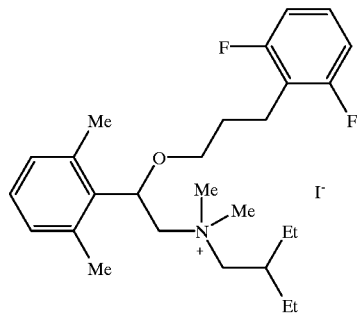

Prepared analogously to Example 5 starting from Example 12; melting point: 105° C.; MS: m/z 432 [(M+H)⁺].

EXAMPLE 16

N-[2-[3-(2,6-difluorophenyl)propoxy]-2-(2,6-dimethylphenyl)ethyl]-N-n-butyl-N,N-dimethylammonium iodide

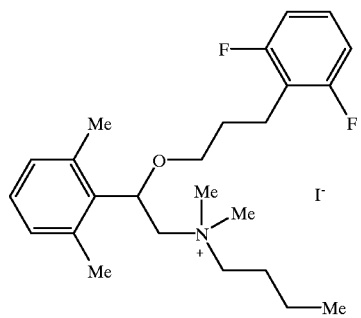

Prepared analogously to Example 5 starting from Example 13; MS: m/z 404 [(M+H)⁺].

EXAMPLE 17

N-[2-[3-(2,6-difluorophenyl)propoxy]-2-(2,6-dimethylphenyl)ethyl]-N-isopropylamine

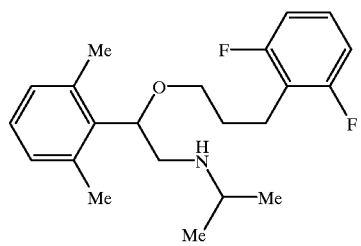

Prepared analogously to Example 3; oil; MS: m/z 362 [(M+H)⁺].

EXAMPLE 18

1-[2-[13-(2,6-difluorophenyl)propoxy]-2-(2,6-dimethylphenyl)ethyl]azepan

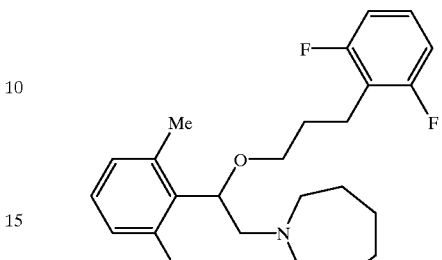

Prepared analogously to Example 6; oil; MS: m/z 402 [(M+H)⁺].

EXAMPLE 19

N-[2-[3-(2,6-difluorophenyl)propoxy]-2-(2,6-dimethylphenyl)ethyl]-N-neopentylamine

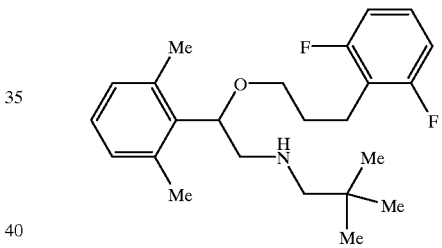

Prepared analogously to Example 3; oil; MS: m/z 390 [(M+H)⁺].

EXAMPLE 20

N-[2-[3-(2,6-difluorophenyl)propoxy]-2-(2,6-dimethylphenyl)ethyl]-N,N-diethylamine

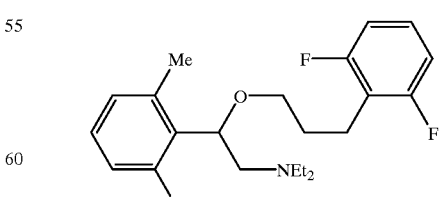

Prepared analogously to Example 2; oil; MS: m/z 376 [(M+H)⁺].

EXAMPLE 21

N-[2-[3-(2,6-difluorophenyl)propoxy]-2-(2,6-dimethylphenyl)ethyl]-N-cyclohexylmethylamine

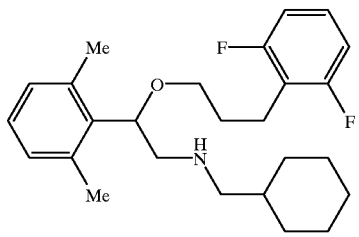

Prepared analogously to Example 3; melting point (hydrochloride): 187° C.; MS: m/z 416 [(M+H)+]. To prepare the hydrochloride of the title compound, the free base is taken up in a little ether and ethereal hydrochloric acid is added dropwise until the precipitation is complete. Then the solvent is removed, the residue is carefully washed with ether and dried.

EXAMPLE 22

N-[2-[3-(2,6-difluorophenyl)propoxy]-2-(2,6-dimethylphenyl)ethyl]-N-isobutylamine

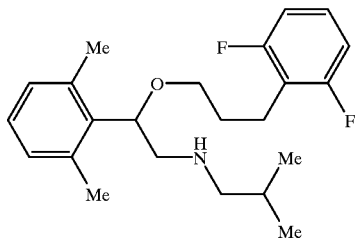

Prepared analogously to Example 3; oil; MS: m/z 376 [(M+H)+].

EXAMPLE 23

N-[2-[3-(2,6-difluorophenyl)propoxy]-2-(2,6-dimethylphenyl)ethyl]-N-benzylamine

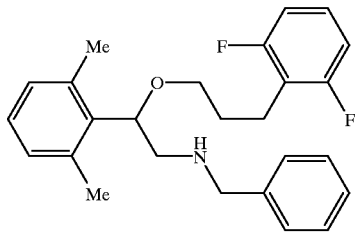

Prepared analogously to Example 3; melting point (hydrochloride): 176° C.; MS: m/z 410 [(M+H)+]. To prepare the hydrochloride of the title compound, the free base is taken up in a little ether and ethereal hydrochloric acid is added dropwise until the precipitation is complete. Then the solvent is removed, the residue is carefully washed with ether and dried.

EXAMPLE 24

N-[2-[3-(2,6-difluorophenyl)propoxy]-2-(2,6-dimethylphenyl)ethyl]-N,N-bis(benzyl)amine

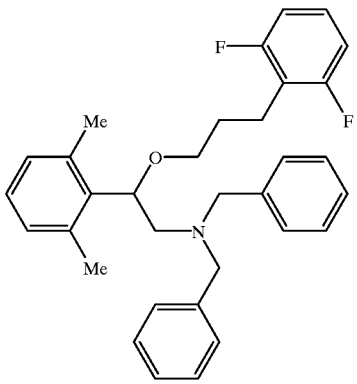

Prepared analogously to Example 2; melting point (hydrochloride): 108° C.; MS: m/z 500 [(M+H)+]. To prepare the hydrochloride of the title compound, the free base is taken up in a little ether and ethereal hydrochloric acid is added dropwise until the precipitation is complete. Then the solvent is removed, the residue is carefully washed with ether and dried.

EXAMPLE 25

N-[2-[3-(2,6-difluorophenyl)propoxy]-2-(2,6-dimethylphenyl)ethyl]-N-(4-isopropenylcyclohexen-1-ylmethyl)amine

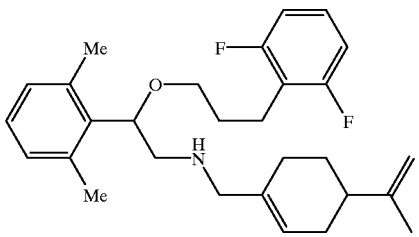

Prepared analogously to Example 3; melting point (hydrochloride): 155° C.; MS: m/z 454 [(M+H)+]. To prepare the hydrochloride of the title compound, the free base is taken up in a little ether and ethereal hydrochloric acid is added dropwise until the precipitation is complete. Then the solvent is removed, the residue is carefully washed with ether and dried.

EXAMPLE 26

N-[2-[3-(2,6-difluorophenyl)propoxy]-2-(2,6-dimethylphenyl)ethyl]-N-(2-methylbutyl)amine

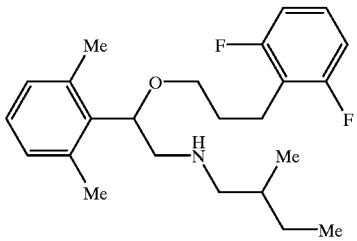

Prepared analogously to Example 3; oil; MS: m/z 390 [(M+H)+].

EXAMPLE 27

N-[2-[3-(2,6-difluorophenyl)propoxy]-2-(2,6-dimethylphenyl)ethyl]-N,N-bis(2-methylbutyl)amine

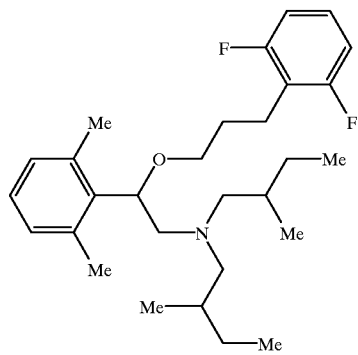

Prepared analogously to Example 2; oil; MS: m/z 460 [(M+H)+].

EXAMPLE 28

N-[2-[3-(2,6-difluorophenyl)propoxy]-2-(2,6-dimethylphenyl)ethyl]-N-neohexylamine

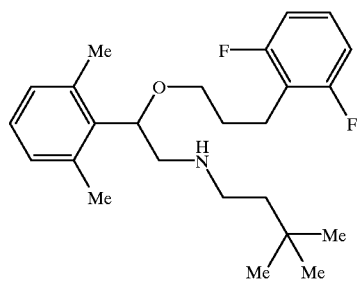

Prepared analogously to Example 3; oil; MS: m/z 404 [(M+H)+].

EXAMPLE 29

N-[2-[3-(2,6-difluorophenyl)propoxy]-2-(2,6-dimethylphenyl)ethyl]-N,N-bis(neohexyl)amine

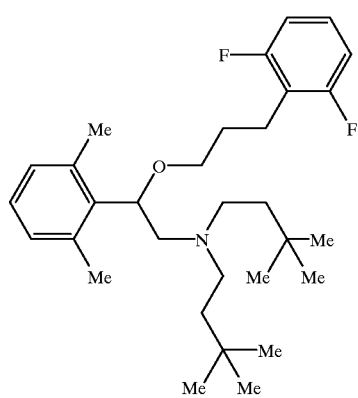

Prepared analogously to Example 2; oil; MS: m/z 488 [(M+H)+].

EXAMPLE 30

N-[2-[3-(2,6-difluorophenyl)propoxy]-2-(2,6-dimethylphenyl)ethyl]-N-(2-trifluoromethylethyl)amine

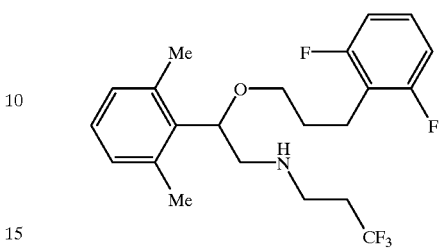

Prepared analogously to Example 3; oil; MS: m/z 416 [(M+H)+].

EXAMPLE 31

N-[2-[3-(2,6-difluorophenyl)propoxy]-2-(2,6-dimethylphenyl)ethyl]-N-cyclohexylamine

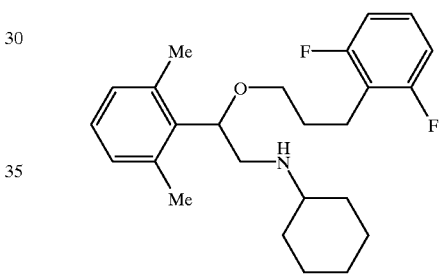

Prepared analogously to Example 3; oil; MS: m/z 402 [(M+H)+].

EXAMPLE 32

N-[2-[3-(2,6-difluorophenyl)propoxy]-2-(2,6-dimethylphenyl)ethyl]-N-isopentylamine

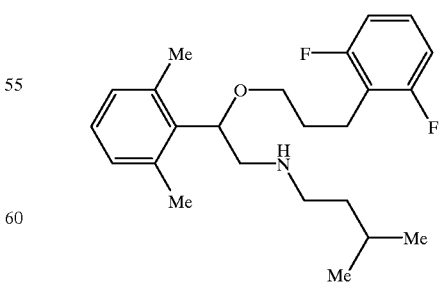

Prepared analogously to Example 3; oil; MS: m/z 390 [(M+H)+].

EXAMPLE 33

N-[2-[3-(2,6-difluorophenyl)propoxy]-2-(2,6-dimethylphenyl)ethyl]-N,N,N-trimethylammonium iodide

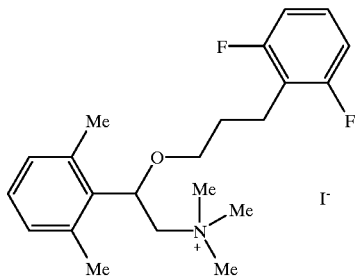

Prepared analogously to Example 5 starting from Example 1; melting point: 190° C.

EXAMPLE 34

[3-(2,6-difluorophenyl)propyl]-[1-(2,6-dimethylphenyl)-2-pyrrolidin-1-ylethyl]amine

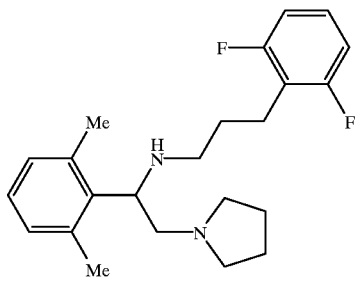

34.1: 3-(2,6-difluorophenyl)propylamine (corresponding to the compound of formula 18)

3.20 g (13.6 mmol) of 2-(3-bromopropyl)-1,3-difluorobenzene (corresponding to Example 1.2.5) is reacted with a solution of 5 g of ammonia in 30 ml of THF in the autoclave for 20 hours at 80° C. The mixture is then evaporated down and the residue is purified by flash chromatography. Yield: 1.01 g, MS: m/z 172 [(M+H)$^+$].

34.2: 1-(2,6-dimethylphenyl)-2-pyrrolidin-1-yl ethanol (corresponding to the compound of formula 16)
Process According to Stage (vii)

647 mg (3.00 mmol) of 1,4-dibromobutane, 1.0 g of potassium carbonate, and 250 mg of potassium iodide are added to a solution of 500 mg (3.00 mmol) of 2-amino-1-(2,6-dimethylphenyl) ethanol (Example 1.3) in 30 ml acetonitrile. The mixture is refluxed for 3 hours. Then the solvent is eliminated and the residue is taken up in dichloromethane. It is filtered, evaporated down, and the crude product is purified by flash chromatography (dichloromethane/ethanol 90:10). Yield 360 mg, melting point: 126° C., MS: m/z 220 [(M+H)$^+$].

34.3: 1-(2,6-dimethylphenyl)-2-pyrrolidin-1-ylethyl methanesulfonate (corresponding to the compound of formula 17)
Process According to Stage (xiv)

219 mg (1.00 mmol) of 1-(2,6-dimethylphenyl)-2-pyrrolidin-1-yl ethanol (Example 34.2) is dissolved in 3 ml of dichloromethane and combined with 250 μl (1.80 mmol) of triethylamine and 105 μl (1.30 mmol) of methanesulfonic acid chloride. The mixture is stirred for 14 hours at ambient temperature, 2 ml of saturated sodium hydrogen carbonate solution is added, the mixture is extracted with dichloromethane, dried, and evaporated down. Yield: 192 mg of brown oil.

34.4: [3-(2,6-difluorophenyl)propyl]-[1-(2,6-dimethylphenyl)-2-pyrrolidin-1-ylethyl]amine
Process According to Stage (xv)

140 mg (0.81 mmol) of 3-(2,6-difluorophenyl)propylamine (Example 34.1) and 2 ml of diisopropylethylamine are added to a solution of 190 mg (0.63 mmol) of 1-(2,6-dimethylphenyl)-2-pyrrolidin-1-ylethyl methanesulfonate (Example 34.3) in 2 ml of acetonitrile. The mixture is stirred for 6 hours at 80° C., evaporated down and the residue is purified by flash chromatography. Yield: 13 mg of yellow oil, MS: m/z 373 [(M+H)$^+$].

EXAMPLE 35

[3-(2,6-difluorophenyl)propyl]-[1-(2,6-dimethylphenyl)-2-piperidin-1-ylethyl]amine

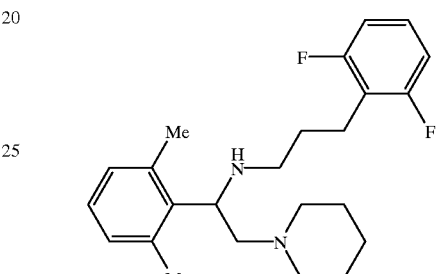

Prepared analogously to Example 34; melting point (hydrochloride): 145° C., MS: m/Z 387 [(M+H)$^+$]. To prepare the hydrochloride of the title compound, the free base is taken up in a little ether and ethereal hydrochloric acid is added dropwise until the precipitation is complete. Then the solvent is removed, the residue is carefully washed with ether and dried.

EXAMPLE 36

1-[2-[2-(2-Fluorophenyl)ethoxy]-2-(2,6-dimethylphenyl)ethyl]piperidine

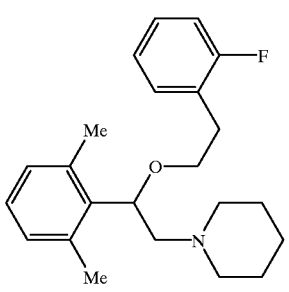

36.1: 2,6-dimethyl-α-bromoacetophenone (corresponding to the compound of formula 13)
Process According to Stage (x)

23.3 g (0.15 mol) of 2,6-dimethylacetophenone, prepared according to Rec. Trav. Chim. Pays-Bas 61 539, 544 (1942), are dissolved in 250 ml of absolute ether, reacted with 7.5 ml (0.15 mol) of bromine within about 30 minutes and stirred for a further 2 hours at ambient temperature. The ethereal solution is washed 2 times with about 100 ml of water, NaHCO$_3$ is added until a pH of 6 is reached and then dried. The ethereal solution is further reacted directly.

36.2: α-N-piperidino-2,6-dimethylacetophenone (corresponding to the compound of formula 14)
Process According to Stage (xi)

The ethereal solution according to Example 36.1 is added dropwise to a solution of 30 ml (0.3 mol) of piperidine in 50 ml of absolute ether and the mixture is then stirred for a further 3 hours at ambient temperature. The precipitate formed is suction filtered and the solvent is eliminated from the ether phase. The residue is immediately reduced.

36.3: 1-(2,6-dimethylphenyl)-2-piperidinoethanol (corresponding to the compound of formula 15)
Process According to Stage (xii)

The crude product according to Example 36.2 is taken up in 300 ml of isopropanol, mixed with 2.3 g (0.06 mol) of $NaBH_4$, refluxed for 3 hours, the same amount of $NaBH_4$ is added to complete the reaction and the mixture is refluxed for a further 3 hours. Then the solvent is eliminated, the residue of about 30 g is divided between water and methylene chloride and the organic phase is dried and evaporated down. After flash chromatography on silica gel using methylene chloride/methanol (95:5) to (90:10) as eluant, 15.1 g of the compound c) are obtained as a light-colored oil. Alternatively, the reduction may be carried out with $LiAlH_4$ in THF, preferably at −60° C.; purification by chromatography can be omitted here.

36.4: 1-[2-[2-(2-fluorophenyl)ethoxy]-2-(2,6-dimethylphenyl)ethyl]piperidine
Process According to Stage (xiii)

2.3 g (0.01 mol) of the ethanolamine according to Example 36.3 and 0.6 g (0.01 mol) of finely powdered KOH are stirred for 15 minutes in DMSO, then stirred with 1.2 g (0.01 mol) of 2-fluorophenylacetylene for 4 hours at 70° C., mixed with water and worked up by extraction with methylene chloride. After the solvent has been eliminated, the residue is subjected to flash chromatography on silica gel with methylene chloride/methanol (95:5) as eluant. The main fraction of 2.5 g thus obtained is hydrogenated in 30 ml of methanol at ambient temperature with 0.5 g $Pd/BaSO_4$ as catalyst under a pressure of 5 bar. The solvent is removed and the residue is subjected to flash chromatography on silica gel with ethyl acetate/cyclohexane (25:75). The clean fraction is mixed with the calculated amount of fumaric acid. There is no salt formation with fumaric acid: after the elimination of the solvent, the title compound is obtained as an amorphous compound.

EXAMPLE 37
1-[2-(2,6-dimethylbenzyloxy)-2-(2,6-dimethylphenyl)ethyl]piperidine

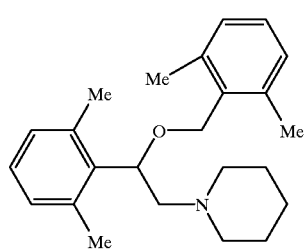

Process According to Stage (xiii)

1.5 g (0.006 mol) of the ethanolamine according to Example 36.3 is dissolved in 30 ml of absolute THF, mixed with 0.9 g (0.0077 mol) of potassium tert-butoxide and stirred for 30 minutes. After the addition of 1.5 g (0.0077 mol) of 2,6-dimethylbenzylbromide, the reaction mixture is stirred for a further 60 minutes at ambient temperature, then the solvent is eliminated and the residue is divided between water and methylene chloride. After being washed and dried, the organic phase is evaporated down and the oily residue of 2.2 g is purified by flash chromatography on silica gel and ethyl acetate/cyclohexane (25:75) as eluant. The oil obtained is converted into the hydrochloride (melting point 185° C.–186° C.).

EXAMPLE 38
1-[2-benzyloxy-2-(2,6-dimethylphenyl)ethyl]piperidine

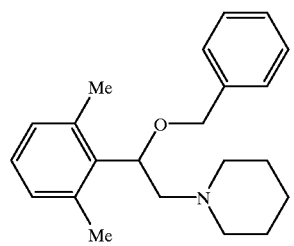

Prepared analogously to Example 37; melting point (hydrochloride): 197° C.–199° C.

EXAMPLE 39
1-[2-(4-bromobenzyloxy)-2-(2,6-dimethylphenyl)ethyl]piperidine

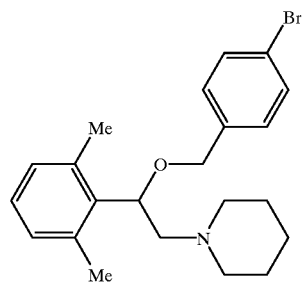

Prepared analogously to Example 37; melting point (hydrochloride): 152° C.–154° C.

EXAMPLE 40
1-[2-(4-chlorobenzyloxy)-2-(2,6-dimethylphenyl)ethyl]piperidine

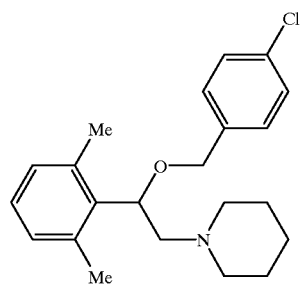

Prepared analogously to Example 37; melting point (hydrochloride): 134° C.–135° C.

EXAMPLE 41

1-[2-(2,6-dichlorobenzyloxy)-2-(2,6-dimethylphenyl)ethyl]piperidine

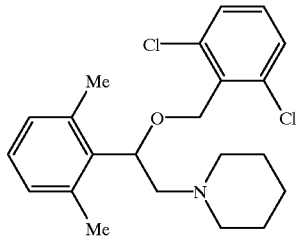

Prepared analogously to Example 37; melting point (hydrochloride): 225° C.–227° C.

EXAMPLE 42

1-[2-(2,6-difluorobenzyloxy)-2-(2,6-dimethylphenyl)ethyl]piperidine

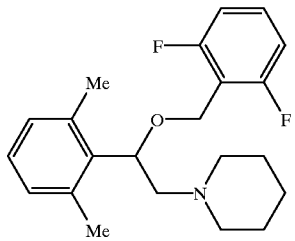

Prepared analogously to Example 37; melting point (hydrochloride): 183° C.–185° C.

EXAMPLE 43

1-[2-(2-chloro-4-bromobenzyloxy)-2-(2,6-dimethylphenyl)ethyl]piperidine

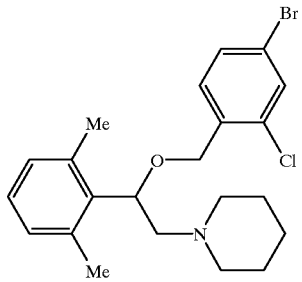

Prepared analogously to Example 37; melting point (hydrochloride): 222° C.–224° C.

EXAMPLE 44

1-[2-[3-(2,6-difluorophenyl)propoxy]-2-(2,6-dimethylphenyl)ethyl]imidazole

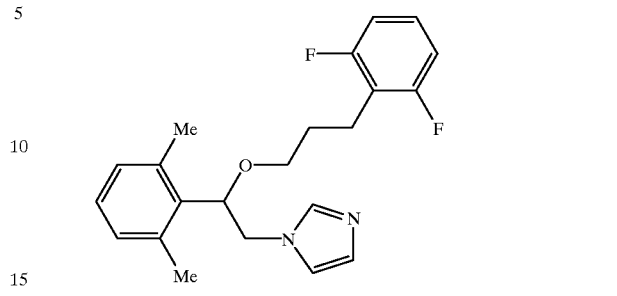

Prepared analogously to Example 37 using sodium hydride as auxiliary base; melting point (hydrochloride): 184° C.–185° C.

EXAMPLE 45

N-[3-(2,6-difluorophenyl)propyl]-[1-(2,6-dimethylphenyl-2-piperidin-1-ylethyl]-N-cyclopropylmethylamine

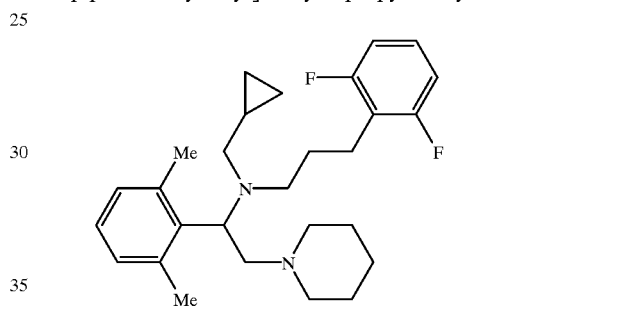

150 mg (0.39 mmol) of [3-(2,6-difluorophenyl)propyl]-[1-(2,6-dimethylphenyl)-2-piperidin-1-ylethyl]amine (corresponds to Example 35) is placed in 3 ml of acetonitrile/DMF 1:1 and 107 mg of potassium carbonate and 20 mg of potassium iodide are added. Then 0.04 ml (0.39 mmol) of bromomethylcyclopropane are added and the mixture is stirred for 16 hours at 75° C. It is then filtered through kieselguhr, the solution is evaporated down, and the residue is purified by flash chromatography (cyclohexane/ethyl acetate 7:3). MS: m/z 441 [(M+H)$^+$].

EXAMPLE 46

N-[3-(2,6-difluorophenylpropyl]-[1-(2,6-dimethylphenyl)-2-piperidin-1-ylethyl]-N-ethylamine

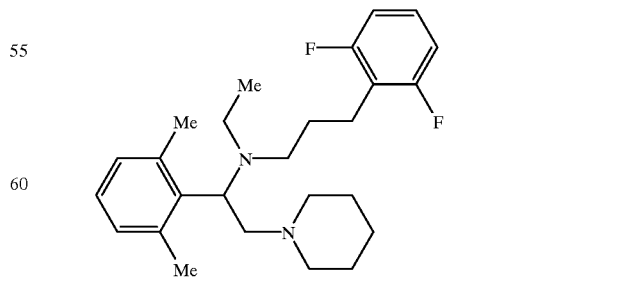

Prepared analogously to Example 45 starting from Example 35; MS: m/z 416 [(M+H)$^+$].

EXAMPLE 47

N-[3-(2,6-difluorophenyl)propyl]-[1-(2,6-dimethylphenyl)-2-piperidin-1-ylethyl]-N-isopentylamine

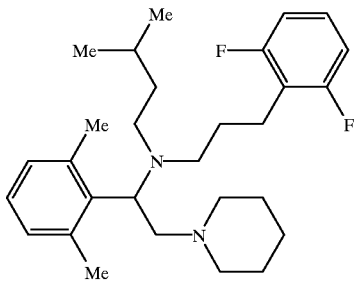

Prepared analogously to Example 45 starting from Example 35; MS: m/z 457 [(M+H)+].

EXAMPLE 48

N-[3-(2,6-difluorophenyl)propyl]-[1-(2,6-dimethylphenyl)-2-piperidin-1-ylethyl]-N-isobutylamine

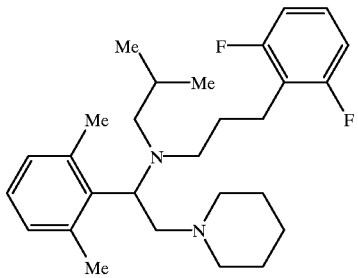

Prepared analogously to Example 45 starting from Example 35; MS: m/z 443 [(M+H)+].

EXAMPLE 49

N-[3-(2,6-difluorophenyl)propyl]-[1-(2,6-dimethylphenyl)-2-pyridin-1-ylethyl]-N-isobutylamine

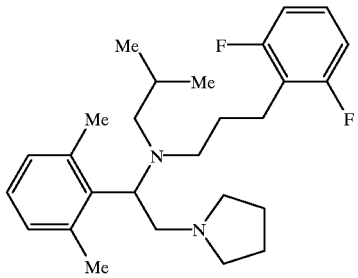

Prepared analogously to Example 45 starting from Example 34; MS: m/z 429 [(M+H)+].

EXAMPLE 50

N-[3-(2,6-difluorophenylpropyl]-[1-(2,6-dimethylphenyl)-2-pyrrolidin-1-ylethyl]-N-isopentylamine

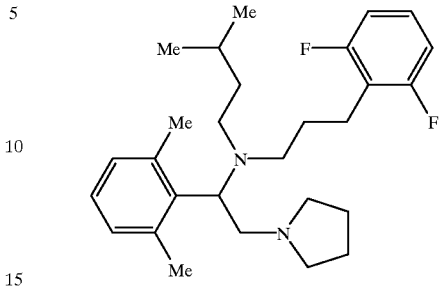

Prepared analogously to Example 45 starting from Example 34; MS: m/z 443 [(M+H)+].

EXAMPLE 51

N-[3-(2,6-difluorophenyl)propyl]-[1-(2,6-dimethylphenyl)-2-pyrrolidin-1-ylethyl]-N-cyclopropylmethylamine

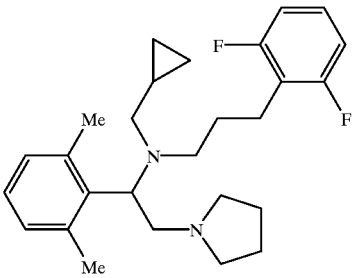

Prepared analogously to Example 45 starting from Example 34; MS: m/z 427 [(M+H)+].

EXAMPLE 52

N-[3-(2,6-difluorophenyl)propyl]-[1-(2,6-dimethylphenyl)-2-piperidin-1-ylethyl]-N-acetylamine

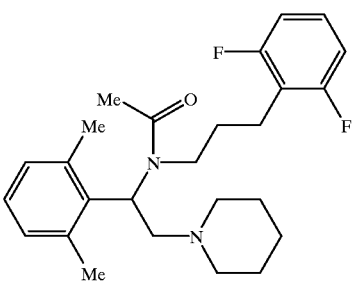

150 mg (0.39 mmol) of [3-(2,6-difluorophenyl)propyl]-[1-(2,6-dimethylphenyl)-2-piperidin-1-ylethyl]amine (corresponds to Example 35) is placed in 3 ml of THF. Then 0.07 ml of DIPEA and 0.02 ml (0.39 mmol) of acetic acid are added; and finally 124.6 mg (0.39 mmol) of TBTU are added. The mixture is then stirred for 6 hours at room temperature, the solvent is eliminated, ethyl acetate and saturated NaHCO₃ solution are added, and the resulting mixture is stirred for 15 minutes. The phases are separated and the organic phase is washed twice more with NaHCO₃ solution and twice with saturated NaCl solution. The organic phase is dried and evaporated down and the residue is purified by flash chromatography (cyclohexane/ethyl acetate 7:3). MS: m/z 429 [(M+H)+].

EXAMPLE 53

N-[3-(2,6-difluorophenyl)propyl]-[1-(2,6-dimethylphenyl)-2-piperidin-1-ylethyl]-N-propionylamine

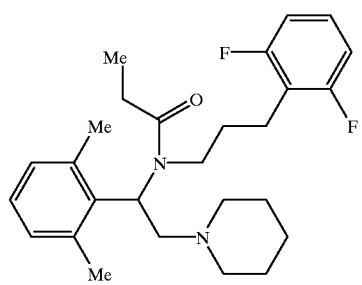

Prepared analogously to Example 52 starting from Example 35; MS: m/z 443 [(M+H)⁺].

EXAMPLE 54

N-[3-(2,6-difluorophenyl)propyl]-[1-(2,6-dimethylphenyl)-2-piperidin-1-ylethyl]-N-formylamine

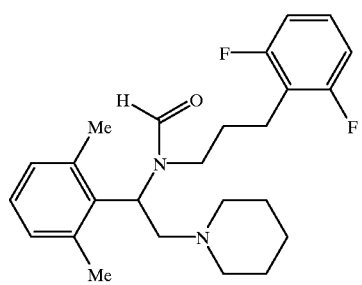

Prepared analogously to Example 52 starting from Example 35; MS: m/z 415 [(M+H)⁺].

EXAMPLE 55

N-[3-(2,6-difluorophenyl)propyl]-[1-(2,6-dimethylphenyl)-2-pyrrolidin-1-ylethyl]-N-formylamine

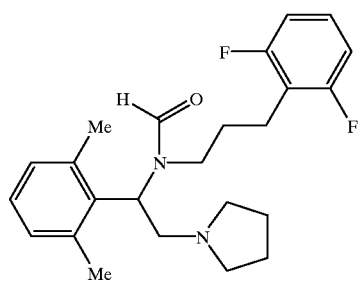

Prepared analogously to Example 52 starting from Example 34; MS: m/z 401 [(M+H)⁺].

EXAMPLE 56

N-[3-(2,6-difluorophenyl)propyl]-[1-(2,6-dimethylphenyl)-2-pyrrolidin-1-ylethyl]-N-acetylamine

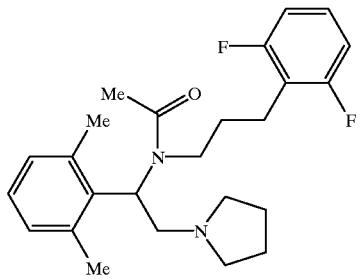

Prepared analogously to Example 52 starting from Example 34; MS: m/z 416 [(M+H)⁺].

EXAMPLE 57

N-[3-(2,6-difluorophenyl)propyl]-[1-(2,6-dimethylphenyl)-2-pyrrolidin-1-ylethyl]-N-propionylamine

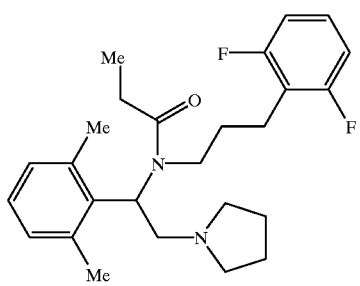

Prepared analogously to Example 52 starting from Example 35; MS: m/z 430 [(M+H)⁺].

EXAMPLE 58

[3-(2,6-difluorophenylpropyl]-[1-(2,6-dimethylphenyl)-2-cyclohexylamino-ethyl]amine

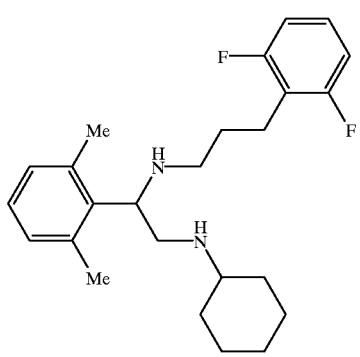

Prepared analogously to Example 34.4, but with reductive amination with cyclohexanone beforehand analogously to Example 2; MS: m/z 400 [(M+H)⁺].

EXAMPLE 59

N-[2-[3-(2,6-difluorophenyl)propoxy]-2-(2,6-dimethylphenyl)ethyl]-N-methyl-N-(1-cyclohexen-4-ylmethyl)amine

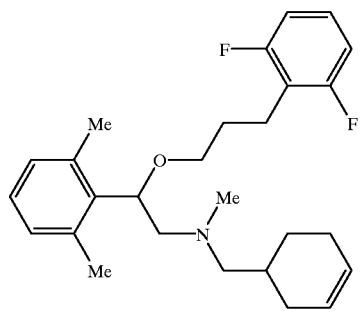

Prepared analogously to Example 5. The monomethyl compound was obtained; oil; MS: m/z 428 [(M+H)+].

EXAMPLE 60

1-[2-[3-(2,6-difluorophenyl)propoxy]-2-(2,4,6-trimethylphenyl)ethyl]-piperidine

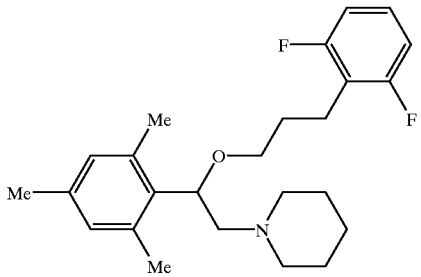

Prepared analogously to Example 6; oil; MS: m/z 401 [(M+H)+].

EXAMPLE 61

1-[2–13-(2,6-difluorophenyl)propoxy]-2-(2,4,6-trimethylphenyl)ethyl]-1-methylpiperidinium iodide

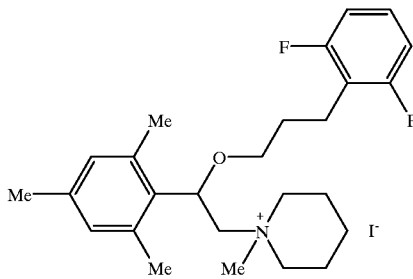

Prepared analogously to Example 7; oil.

EXAMPLE 62

[2-[3-(2,6-difluorophenyl)propoxy]-2-(2,4,6-trimethylphenyl)ethyl]-dimethylamine

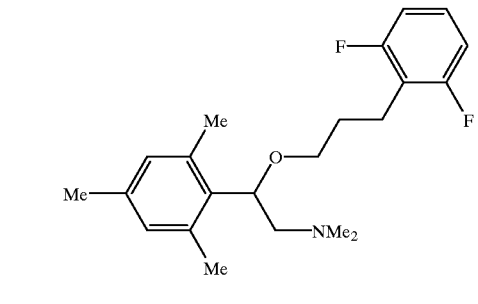

Prepared analogously to Example 8; oil; MS: m/z 401 [(M+H)+].

EXAMPLE 63

[2-[3-(2,6-difluorophenylpropoxy]-2-(2,4,6-dimethylphenyl)ethyl]amine

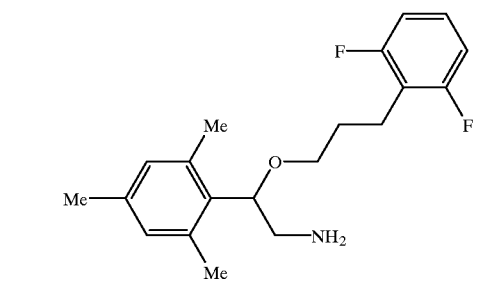

Prepared analogously to Example 1; oil; MS: m/z 334 [(M+H)+].

EXAMPLE 64

[2-[3-(2,6-difluorophenyl)propoxy]-2-(2,4,6-dimethylphenyl)ethyl]trimethyl-ammonium iodide

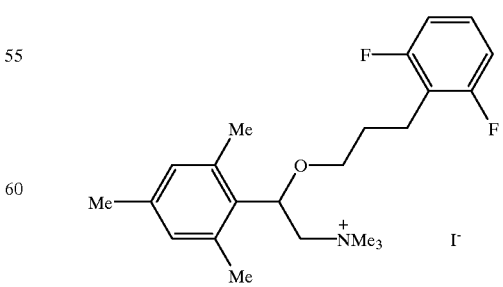

Prepared analogously to Example 5; yellow crystals.

EXAMPLE 65

N-[2-[3-(2,6-difluorophenyl)propoxy]-2-(2,6-dimethylphenylethyl]-N-(3-phenylpropyl)-N,N-dimethylammonium iodide

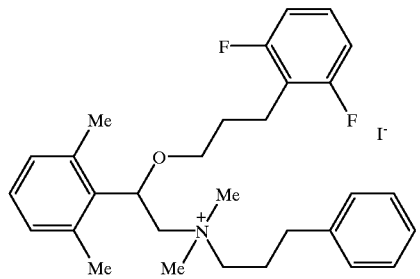

Prepared analogously to Example 5; oil; MS: m/z 466 [(M+H)+].

EXAMPLE 66

N-[2-[3-(2,6-difluorophenyl)propoxy]-2-(2,6-dimethylphenyl)ethyl]-N-methyl-N-cyclohexylamine

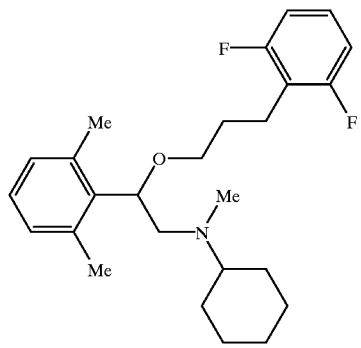

Prepared analogously to Example 4; oil; MS: m/z 416 [(M+H)+].

EXAMPLE 67

N-[2-[3-(2,6-difluorophenyl)propoxy]-2-(2,6-dimethylphenyl)ethyl]-N-n-propylamine

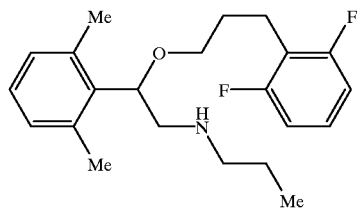

Prepared analogously to Example 3; oil; MS: m/z 362 [(M+H)+].

EXAMPLE 68

N-[2-[3-(2,6-difluorophenyl)propoxy]-2-(2,6-dimethylphenyl)ethyl]-N-(3-phenylethyl)amine

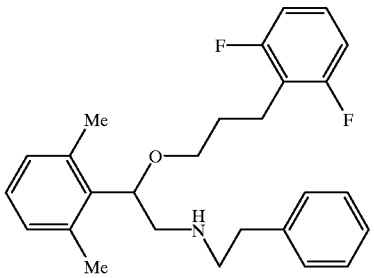

Prepared analogously to Example 3; oil; MS: m/z 424 [(M+H)+].

EXAMPLE 69

N-[2-[3-(2,6-difluorophenyl)propoxy]-2-(2,6-dimethylphenyl)ethyl]-N,N-bis(3-phenylpropyl)amine

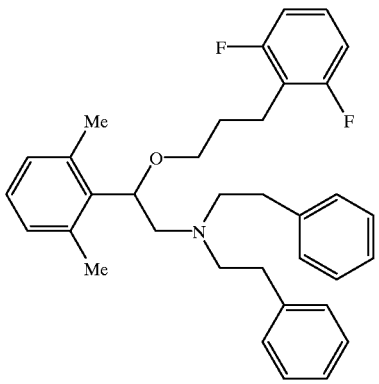

Prepared analogously to Example 2; oil; MS: m/z 528 [(M+H)+].

EXAMPLE 70

N-[2-[3-(2,6-difluorophenylpropoxy]-2-(2,6-dimethylphenyl)ethyl]-N-(2-methylbut-1-yl)-N-ethylamine

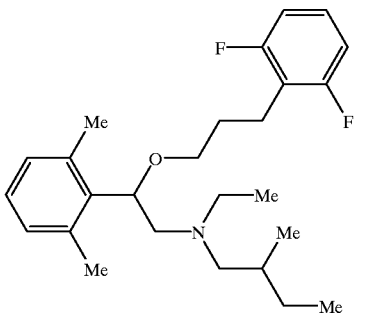

Prepared analogously to Example 5; oil; MS: m/z 418 [(M+H)+].

EXAMPLE 71

N-[2-[3-(2,6-difluoropheny)propoxy]-2-(2,6-dimethylphenyl)ethyl]-N-(3,3-dimethylbut-1-yl)-N-ethylamine

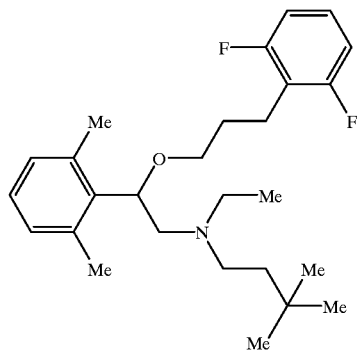

Prepared analogously to Example 5; oil; MS: m/z 432 [(M+H)⁺].

EXAMPLE 72

N-[2-[3-(2,6-difluorophenyl)propoxy]-2-(2,6-dimethylphenyl)ethyl]-N-benzyl-N-ethylamine

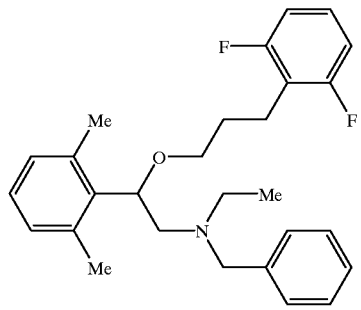

Prepared analogously to Example 5; oil; MS: m/z 437 [(M+H)⁺].

EXAMPLE 73

N-[2-[3-(2,6-difluorophenyl)propoxy]-2-(2,6-dimethylphenyl)ethyl]-N-isobutyl-N-ethylamine

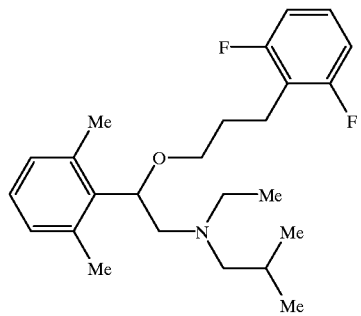

Prepared analogously to Example 5; oil; MS: m/z 404 [(M+H)⁺].

EXAMPLE 74

N-[2-[3-(2,6-difluorophenyl)propoxy]-2-(2,6-dimethylphenyl)ethyl]-N-(2,2-dimethylprop-1-yl)-N-ethylamine

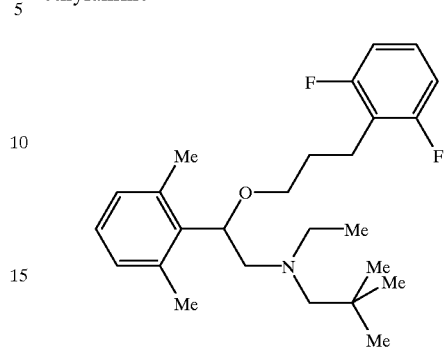

Prepared analogously to Example 5; oil; MS: m/z 418 [(M+H)⁺].

EXAMPLE 75

N-[2-[3-(2,6-difluorophenyl)propoxy]-2-(2,6-dimethylphenyl)ethyl]-N-(2,2-dimethylprop-1-yl)-N,N-dimethylammonium iodide

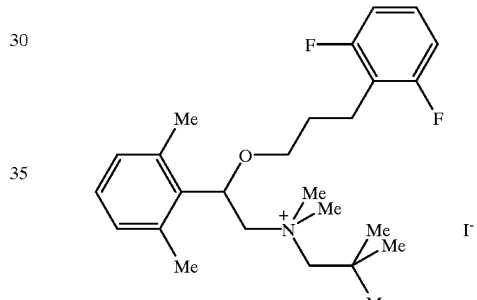

Prepared analogously to Example 5; oil; MS: m/z 418 [(M+H)⁺].

EXAMPLE 76

N-[2-[3-(2,6-difluorophenyl)propoxy]-2-(2,6-dimethylphenyl)ethyl]-N-cyclohexyl-N,N-dimethylammonium iodide

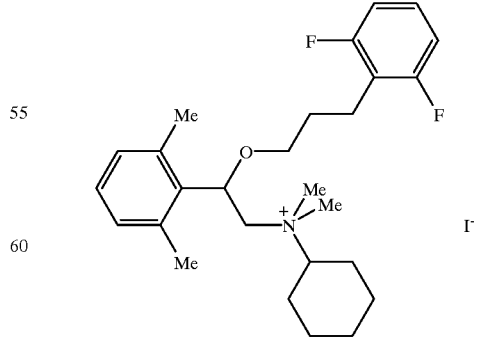

Prepared analogously to Example 5; oil; MS: m/z 430 [M⁺].

EXAMPLE 77

N-[2-[3-(2,6-difluorophenyl)propoxy]-2-(2,6-dimethylphenyl)ethyl]-N-(2-trifluormethylethyl)-N,N-dimethylammonium iodide

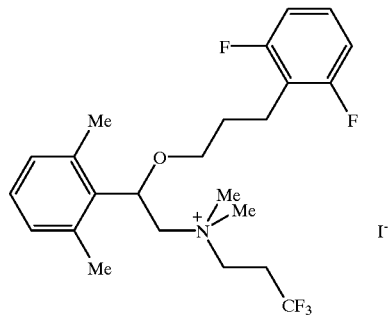

Prepared analogously to Example 5; oil; MS: m/z 444 [(M+H)$^+$].

EXAMPLE 78

N-[2-[3-(2,6-difluorophenyl)propoxy]-2-(2,6-dimethylphenyl)ethyl]-N-(4-isopropenylcyclohexen-1-ylmethyl)-N,N-dimethylammonium iodide

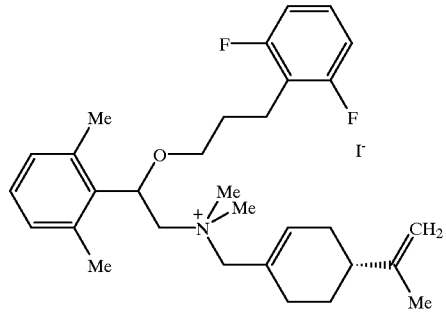

Prepared analogously to Example 5; oil; MS: m/z 482 [M$^+$].

EXAMPLE 79

N-[2-[3-(2,6-difluorophenyl)propoxy]-2-(2,6-dimethylphenyl)ethyl]-N-ethylamine

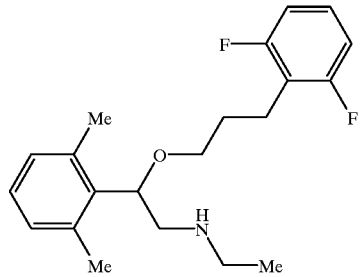

Prepared analogously to Example 3; oil; MS: m/z 348 [(M+H)$^+$].

EXAMPLE 80

N-[2-[3-(2,6-difluorophenylpropoxy]-2-(2,6-dimethylphenyl)ethyl]-N-(3-phenylpropyl)amine

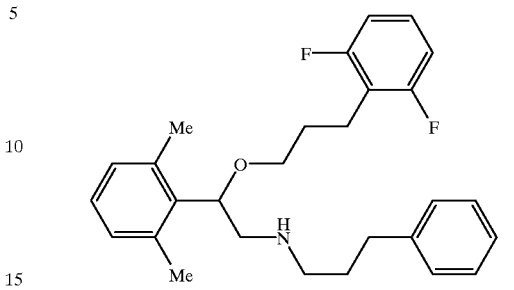

Prepared analogously to Example 3; oil; MS: m/z 438 [(M+H)$^+$].

EXAMPLE 81

N-[2-[3-(2,6-difluorophenylpropoxy]-2-(2,6-dimethylphenyl)ethyl]-N-(4-penten-1-yl)amine

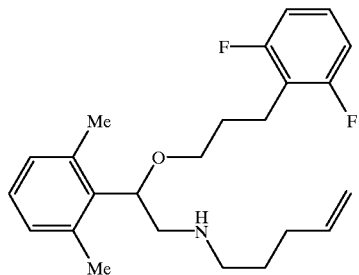

Prepared analogously to Example 3; melting point: 116° C.; MS: m/z 338 [(M+H)$^+$].

EXAMPLE 82

1-[2-[3-(2,6-difluorophenyl)propoxy]-2-(2,6-dimethylphenyl)ethyl]-1-methylpiperidinium iodide

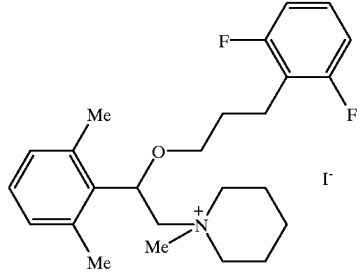

Prepared analogously to Example 7; melting point: 130 (decomp.); MS: m/z 402 [M$^+$].

The compounds according to the invention may be administered by oral, transdermal, intrathecal, or parenteral route, or by inhalation and occur as active ingredients in conventional preparations. The compounds according to the invention may be used on their own or in conjunction with other active substances according to the invention, optionally also in conjunction with other pharmacologically active substances. Suitable preparations include for example tablets, capsules, suppositories, solutions, elixirs, emulsions, or dis persible powders. Suitable tablets may be obtained, for example, by mixing the active substance(s) with known excipients, for example inert diluents such as calcium carbonate, calcium phosphate, or lactose, disintegrants such as corn starch or alginic acid, binders such as starch or gelatine, lubricants such as magnesium stearate or talc, and/or agents for delaying release, such as carboxymethyl cellulose, cellulose acetate phthalate, or polyvinyl acetate. The tablets may also comprise several layers.

The following are examples of pharmaceutical preparations containing the active substance:

A. TABLETS

| Component | Amount per tablet (mg) |
| --- | --- |
| active substance of general formula 1 or 1-Y | 20 |
| lactose | 190 |
| magnesium stearate | 1 |

B. INJECTABLE SOLUTION

| Component | Amount |
| --- | --- |
| active substance of general formula 1 or 1-V | 0.3 mg |
| sodium chloride | 0.8 g |
| benzalkonium chloride | 0.01 mg |
| water for injection | ad 100 ml |

A solution similar to that shown above is suitable for nasal administration in a spray, or in conjunction with a device which produces an aerosol with a particle size preferably between 2 and 6 $\mu$M, for administration via the lungs.

Solution for Infusion

A 5% by weight xylitol or saline solution which contains the active substance in a concentration of 2 mg/ml, for example, is adjusted to a pH of about 4 using a sodium acetate buffer. Infusible solutions of this kind may contain an active substance according to general formula 1 in an amount, based on the total mass of the pharmaceutical preparation, in the range from 0.001 wt. % to 5 wt. %, preferably in the range from 0.001 wt. % to 3 wt. %, and most preferably in the range from 0.01 to 1 wt. %.

Capsules for Inhalation

The active substance according to general formula 1 in micronised form is packed into hard gelatine capsules (particle size substantially between 2 and 6 $\mu$M), optionally with the addition of micronised carrier substances, such as lactose. It can be inhaled using conventional equipment for powder inhalation. Between 0.2 and 20 mg of active substance and 0 to 40 mg of lactose, for example, are packed into each capsule.

C. AEROSOL FOR INHALATION

| Component | Amount |
| --- | --- |
| active substance of general formula 1 or 1-Y | 1 part |
| soya lecithin | 0.2 parts |
| propellant gas mixture | ad 100 parts |

We claim:
1. A compound of formula 1

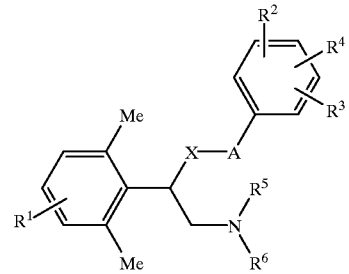

wherein:
$R^1$ is hydrogen, hydroxy, $CF_3$, $NO_2$, CN, halogen, $C_1$–$C_8$-alkyl, or $C_1$–$C_8$-alkoxy;

$R^2$, $R^3$, and $R^4$ independently of one another are hydrogen, $C_1$–$C_8$-alkyl, hydroxy, $NO_2$, CN, $C_1$–$C_8$-alkoxyl, $CF_3$, or halogen;

$R^5$ and $R^6$ independently of one another are hydrogen or a group consisting of $C_1$–$C_8$-alkyl, $C_2$–$C_8$-alkenyl, $C_3$–$C_8$-alkynyl, $C_3$–$C_8$-cycloalkyl, $C_3$–$C_8$-cycloalkyl-$C_1$–$C_6$-alkylene, $C_5$–$C_8$-cyclokenyl, $C_5$–$C_8$-cycloalkenyl-$C_1$–$C_6$-alkylene, $C_6$–$C_{10}$-aryl, and $C_6$–$C_{10}$-aryl-$C_1$–$C_6$-alkylene, each optionally substituted by a group consisting of $C_1$–$C_6$-alkyl, $C_2$–$C_6$-alkenyl, halogen, $C_1$–$C_6$-alkyloxy, —$NH_2$, —NH($C_1$–$C_4$-alkyl), —N($C_1$–$C_4$-alkyl)$_2$, hydroxy, =O, —COOH, —CO—O$C_1$–$C_4$-alkyl, —$CONH_2$, —CONH($C_1$–$C_4$-alkyl), —CON($C_1$–$C_4$-alkyl)$_2$, and $CF_3$, or $R^5$ and $R^6$ together with the nitrogen atom are a saturated or unsaturated 5-, 6-, 7-, or 8-membered heterocyclic group optionally containing one or two further heteroatoms consisting of sulfur, oxygen, and nitrogen, and optionally mono-, di-, or trisubstituted by a group consisting of $C_1$–$C_4$-alkyl, hydroxy, =O, —COOH, —CO—O$C_1$–$C_4$-alkyl, —$CONH_2$, —CONH($C_1$–$C_4$-alkyl), —CON($C_1$–$C_4$-alkyl)$_2$, halogen, and benzyl;

X is oxygen, —NH—, —N(CHO)—, —N(CO—$C_1$–$C_6$-alkyl), —N($C_1$–$C_6$-alkyl), or —N($C_3$–$C_6$-cycloalkyl-$C_1$–$C_4$-alkylene); and A is a group consisting of $C_1$–$C_6$-alkylene, $C_2$–$C_6$-alkenylene, and $C_3$–$C_6$-alkynylene, or a free base or pharmacologically acceptable acid addition salt thereof.

2. The compound of formula 1 according to claim 1, wherein:

$R^1$ is hydrogen, halogen, $C_1$–$C_6$-alkyl, $CF_3$, or methoxy;

$R^2$, $R^3$, and $R^4$ independently of one another are hydrogen, $C_1$–$C_6$-alkyl, $C_1$–$C_6$-alkyloxy, $CF_3$, or halogen;

$R^5$ and $R^6$ independently are hydrogen or a group consisting of $C_1$–$C_6$-alkyl. $C_2$–$C_6$-alkenyl, $C_3$–$C_6$-alkynyl, $C_3$–$C_6$-cycloalkyl-$C_1$–$C_6$-alkylene, $C_5$–$C_6$-cycloalkenyl, $C_5$–$C_6$-cycloalkenyl-$C_1$–$C_6$-alkylene, phenyl, and phenyl-$C_2$–$C_4$-alkenyl, halogen, $C_1$–$C_{14}$-alkyloxy, hydroxy, —$CONH_2$, =O, and $CF_3$, or $R^5$ and $R^6$ together with the nitrogen atom are a saturated or unsaturated 5-, 6-, or 7-membered heterocyclic group optionally containing one or two further heteroatoms consisting of sulfur, oxygen, and nitrogen and optionally mono-, di-, or trisubstituted by $C_1$–$C_4$-alkyl, hydroxy, or —$CONH_2$;

X is oxygen, —NH—, —N(CHO)—, —N(CO—$C_1$–$C_5$-alkyl), or —N($C_3$–$C_6$-cycloalkyl-$C_1$–$C_4$-alkylene); and A is $C_1$–$C_5$-alkylene, $C_2$–$C_4$-alkenylene, or $C_3$–$C_{14}$-alkynylene, or a free base or pharmacologically acceptable acid addition salt thereof.

3. The compound of formula 1 according to claim 2, wherein:

$R^1$ is hydrogen, $C_1$–$C_4$-alkyl, or $CF_3$;

$R^2$, $R^3$, and $R^4$ independently of one another are hydrogen, $C_1$–$C_4$-alkyl, $CF_3$, or halogen;

$R^5$ and $R^6$ independently of one another are hydrogen, $C_1$–$C_6$-alkyl, $CF_3$–$C_1$–$C_6$-alkylene, $C_2$–$C_6$-alkenyl, $C_3$–$C_6$-alkynyl, $C_3$–$C_6$-cycloalkyl, $C_3$–$C_6$-cycloalkyl-$C_1$–$C_6$-alkylene, cyclohexenyl, cyclohexenyl-$C_1$–$C_6$-alkylene, propenyl-cyclohexenylene-$C_1$–$C_6$-alkylene, phenyl, or phenyl-$C_1$–$C_6$-alkylene, or $R^5$ and $R^6$ together with the nitrogen atom are a saturated or unsaturated 5-, 6-, or 7-membered heterocyclic group, which optionally contains another nitrogen atom and optionally mono-, di-, or trisubstituted by $C_1$–$C_4$-alkyl, hydroxy, —$CONH_2$;

X is oxygen, —NH—, —N(CHO)—, —N(CO-methyl), —N(CO-ethyl), —N($C_1$–$C_5$-alkyl), or —N($C_3$–$C_6$-cycloalkyl-methylene); and A is —$CH_2$—, —$CH_2$—$CH_2$—, or —$CH_2$—$CH_2$—$CH_2$—, or a free base or pharmacologically acceptable acid addition salt thereof.

4. A compound of formula 1 according to claim 3, wherein $R^1$ is hydrogen or methyl;

$R^2$ and $R^3$ independently of one another are hydrogen, methyl, fluorine, chlorine, or bromine;

$R^4$ is hydrogen, fluorine, chlorine, or bromine;

$R^5$ and $R^6$ independently of one another are hydrogen, $C_1$–$C_6$-alkyl, $CF_3$—$C_1$–$C_6$-alkylene, $C_2$–$C_6$-alkenyl, $C_3$–$C_6$-cycloalkyl, cyclohexyl, $C_3$–$C_6$-cycloalkyl-$C_1$–$C_6$-alkylene, cyclohexenyl, cyclohexenyl-$C_1$–$C_6$-alkylene, or $R^5$ and $R^6$ together with the nitrogen atom are a heterocyclic group consisting of pyrrolidine, piperidine, 1,2,3,6-tetrahydropyridine, and azepan;

X oxygen, —NH—, —N(CHO)—, —N(CO-methyl), —N(CO-ethyl), —N(methyl), —N(ethyl), —N(propyl), —N(butyl), —N(pentyl), or —N(cyclopropylmethylene); and A is —$CH_2$—, —$CH_2$—$CH_2$—, or —$CH_2$—$CH_2$—$CH_2$—, or a free base or pharmacologically acceptable acid addition salt thereof.

5. The compound of formula 1 according to claim 4, wherein:

$R^5$ and $R^6$ independently of one another are hydrogen, methyl, propyl, butyl, hexyl, cyclopropylmethyl, or cyclohexenemethyl, or $R^5$ and $R^6$ together with the nitrogen atom are a heterocyclic group consisting of pyrrolidine, piperidine, 1,2,3,6-tetrahydropyridine, and azepan; and X is oxygen, —NH—, —N(CHO)—, —N(CO-methyl), —N(CO-ethyl), —N(ethyl), —N(propyl), —N(butyl), —N(pentyl), or —N(cyclopropylmethylene), or a free base or pharmacologically acceptable acid addition salt thereof.

6. The compound of formula 1 according to claim 4, wherein:

$R^2$ and $R^3$ independently of one another are hydrogen or fluorine;

$R^4$ is hydrogen;

$R^5$ and $R^6$ independently of one another are hydrogen, butyl, hexyl, or cyclohexenemethyl, or $R^5$ and $R^6$ together with the nitrogen atom are piperidine and 1,2,3,6-tetrahydropyridine;

X is oxygen or —NH—; and

A is —$CH_2$—$CH_2$— or —$CH_2$—$CH_2$—$CH_2$—, or a free base or pharmacologically acceptable acid addition salt thereof.

7. A compound of formula 1 according to one of claims 1 to 6, wherein $R^1$ is hydrogen and $R^2$ and $R^3$ are in the ortho position with respect to each other.

8. A compound of formula 1 according to one of claims 1 to 6, wherein $R^1$ is methyl and $R^2$ and $R^3$ are in the ortho position with respect to each other.

9. A quaternary ammonium compound of formula 1-Y

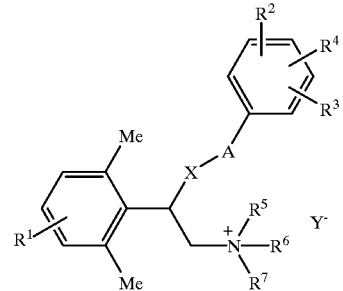

1-Y wherein:

$R^1$ is hydrogen, hydroxy, $CF_3$, $NO_2$, CN, halogen, $C_1$–$C_8$-alkyl, or $C_1$–$C_1$-alkoxy;

$R^2$, $R^3$, and $R^4$ independently of one another are hydrogen, $C_1$–$C_8$-alkyl, hydroxy, $NO_2$, CN, $C_1$–$C_8$-alkyloxy, $CF_3$, or halogen;

$R^5$ and $R^6$ independently of one another are a group consisting of $C_1$–$C_8$-alkyl, $C_2$–$C_8$-alkenyl, $C_3$–$C_8$-alkynyl, $C_3$–$C_8$-cycloalkyl, $C_3$–$C_8$-cycloalkyl-$C_1$–$C_6$-alkylene, $C_5$–$C_8$-cycloalkenyl, $C_5$–$C_8$-cycloalkenyl-$C_1$–$C_6$-alkylene, $C_6$–$C_{10}$-aryl, and $C_6$–$C_{10}$-aryl-$C_1$–$C_6$-alkylene, each optionally substituted by a group consisting of $C_1$–$C_6$-alkyl, $C_2$–$C_6$-alkenyl, halogen, $C_1$–$C_6$-alkyloxy, —$NH_2$, —NH($C_1$–$C_4$-alkyl), —N($C_1$–$C_4$-alkyl)$_2$, hydroxy, =O, —COOH, —CO—$OC_1$–$C_4$-alkyl, —$CONH_2$, —CONH($C_1$–$C_4$-alkyl), —CON($C_1$–$C_4$-alkyl)$_2$, and $CF_3$, or $R^5$ and $R^6$ together with the nitrogen atom are a saturated or unsaturated 5-, 6-, 7-, or 8-membered heterocyclic group optionally containing one or two further heteroatoms consisting of sulfur, oxygen, and nitrogen, and optionally mono-, di-, or trisubstituted by a group consisting of $C_1$–$C_4$-alkyl, hydroxy, =O, —COOH, —CO—$OC_1$–$C_4$-alkyl, —$CONH_2$, —CONH($C_1$–$C_4$-alkyl), —CON($C_1$–$C_4$-alkyl)$_2$, halogen, and benzyl;

$R^7$ is $C_1$–$C_4$-alkyl;

X is oxygen, —NH—, —N(CHO)—, —N(CO—$C_1$–$C_6$-alkyl), —N($C_1$–$C_6$-alkyl), or —N($C_3$–$C_6$-cycloalkyl-$C_1$–$C_4$-alkylene); and $Y^-$ is a halide group;

A is a group consisting of $C_1$–$C_6$-alkylene, $C_2$–$C_6$-alkenylene, and $C_3$–$C_6$-alkynylene, each optionally substituted by a group consisting of halogen, =O, and hydroxy, or a free base or pharmacologically acceptable acid addition salt thereof.

10. The compound of formula 1-Y according to claim 9, wherein:

$R^1$ is hydrogen, halogen, $C_1$–$C_6$-alkyl, $CF_3$, or methoxy;

$R^2$, $R^3$, and $R^4$ independently of one another are hydrogen, $C_1$–$C_6$-alkyl, $C_1$–$C_6$-alkyloxy, $CF_3$, or halogen;

$R^5$ and $R^6$ independently of one another are a group consisting of $C_1$–$C_6$-alkyl, $C_2$–$C_6$-alkenyl, $C_3$–$C_6$-alkynyl, $C_3$–$C_6$-cycloalkyl, $C_3$–$C_6$-cycloalkyl-$C_1$–$C_6$-alkylene, $C_5$–$C_6$-cycloalkenyl, $C_5$–$C_6$-cycloalkenyl-$C_1$–$C_6$-alkylene, phenyl, and phenyl-$C_1$–$C_6$-alkylene, each optionally substituted by a group consisting of $C_1$–$C_4$-alkyl, $C_2$–$C_4$-alkenyl, halogen, $C_1$–$C_4$-alkyloxy, hydroxy, —$CONH_2$, =O, and $CF_3$, or $R^5$ and $R^6$ together with the nitrogen atom are a saturated or unsaturated 5-, 6-, or 7-membered heterocyclic group optionally containing one or two further heteroatoms consisting of sulfur, oxygen, and nitrogen and optionally mono-, di-, or trisubstituted by $C_1$–$C_4$-alkyl, hydroxy, or —$CONH_2$;

X is oxygen, —NH—, —N(CHO)—, —N(CO—$C_1$–$C_5$-alkyl), —N($C_1$–$C_5$-alkyl), or —N($C_3$–$C_6$-cycloalkyl-$C_1$–$C_4$-alkylene); and A is $C_1$–$C_5$-alkylene, $C_2$–$C_4$-alkenylene, or $C_3$–$C_4$-alkynylene.

11. The compound of formula 1-Y according to claim 10, wherein:

$R^1$ is hydrogen, $C_1$–$C_4$-alkyl, or $CF_3$;

$R^2$, $R^3$, and $R^4$ independently of one another are hydrogen, $C_1$–$C_4$-alkyl, $CF_3$, or halogen;

$R^5$ and $R^6$ independently of one another are $C_1$–$C_6$-alkyl, $CF_3$–$C_1$–$C_6$-alkylene, $C_2$–$C_6$-alkenyl, $C_3$–$C_6$-alkynyl, $C_3$–$C_6$-cycloalkyl, $C_3$–$C_6$-cycloalkyl-$C_1$–$C_6$-alkylene, cyclohexenyl, cyclohexenyl-$C_1$–$C_6$-alkylene, propenyl-cyclohexenylene-$C_1$–$C_6$-alkylene, phenyl, or phenyl-$C_1$–$C_6$-alkylene, or $R^5$ and $R^6$ together with the nitrogen atom are a saturated or unsaturated 5-, 6-, or 7-membered heterocyclic group optionally containing another nitrogen atom and optionally mono-, di-, or trisubstituted by $C_1$–$C_4$-alkyl, hydroxy, or —$CONH_2$;

X is oxygen, —NH—, —N(CHO)—, —N(CO-methyl), —N(CO-ethyl), —N($C_1$–$C_5$-alkyl), or —N($C_3$–$C_6$-cycloalkyl-methylene); and A is —$CH_2$—, —$CH_2$—$CH_2$—, or —$CH_2$—$CH_2$—$CH_2$—.

12. The compound of formula 1-Y according to claim 11, wherein:

$R^1$ is hydrogen;

$R^2$ and $R^3$ independently of one another are hydrogen, methyl, fluorine, chlorine, or bromine;

$R^4$ is hydrogen, fluorine, chlorine, or bromine;

$R^5$ and $R^6$ independently of one another are $C_1$–$C_6$-alkyl, $CF_3$–$C_1$–$C_6$-alkylene, $C_2$–$C_6$-alkenyl, $C_3$–$C_6$-cycloalkyl, cyclohexyl, $C_3$–$C_6$-cycloalkyl-$C_1$–$C_6$-alkylene, cyclohexenyl, cyclohexenyl-$C_1$–$C_6$-alkylene, or $R^5$ and $R^6$ together with the nitrogen atom are a heterocyclic group consisting of pyrrolidine, piperidine, 1,2,3,6-tetrahydropyridine, and azepan;

X oxygen, —NH—, —N(CHO)—, —N(CO-methyl), —N(CO-ethyl), —N(methyl), —N(ethyl), —N(propyl), —N(butyl), —N(pentyl), or —N(cyclopropylmethylene); and A is —$CH_2$—, —$CH_2$—$CH_2$—, or —$CH_2$—$CH_2$—$CH_2$—.

13. The compound of formula 1-Y according to claim 12, wherein:

$R^5$ and $R^6$ independently of one another are methyl, propyl, butyl, hexyl, cyclopropylmethyl, or cyclohexenemethyl, or $R^5$ and $R^6$ together with the nitrogen atom are a heterocyclic group consisting of pyrrolidine, piperidine, 1,2,3,6-tetrahydropyridine, and azepan; and X is oxygen, —NH—, —N(CHO)—, —N(CO-methyl), —N(CO-ethyl), —N(ethyl), —N(propyl), —N(butyl), —N(pentyl), or —N(cyclopropylmethylene).

14. The compound of formula 1-Y according to claim 12, wherein:

$R^2$ and $R^3$ independently of one another are hydrogen or fluorine;

$R^4$ is hydrogen;

$R^5$ and $R^6$ independently of one another are butyl, hexyl, or cyclohexenemethyl, or $R^5$ and $R^6$ together with the nitrogen atom are piperidine and 1,2,3,6-tetrahydropyridine;

X is oxygen or —NH—; and

A is —$CH_2$—$CH_2$— or —$CH_2$—$CH_2$—$CH_2$—.

15. A compound of formula 1-Y according to one of claims 9 to 14 wherein $R^1$ is hydrogen and $R^2$ and $R^3$ are in the ortho position with respect to each other.

16. A compound of formula 1-Y according to one of claims 9 to 14 wherein $R^1$ is methyl and $R^2$ and $R^3$ are in the ortho position with respect to each other.

17. A method for making the compound of formula 1 according to one of claims 1 to 9

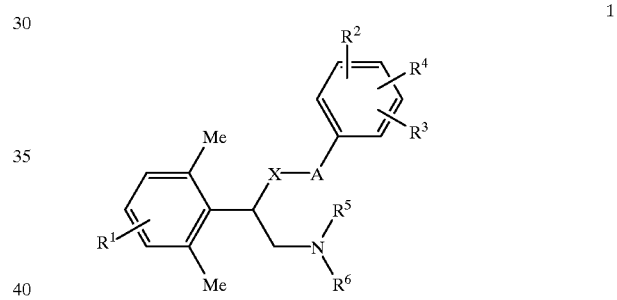

1 wherein the groups A, $R^1$, $R^2$, $R^3$, $R^4$, $R^5$, and $R^6$ have the meanings given in the respective claims 1 to 9 and wherein X is oxygen, the process comprising:

(a) reacting a compound of formula 6

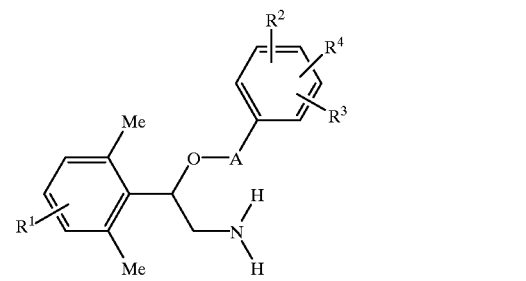

6 wherein the groups A, $R^1$, $R^2$, $R^3$, and $R^4$ have the meanings given above, in an organic solvent in the presence of an inorganic or organic base with a suitable alkylating agent having an alkyl group of $R^5$ and $R^6$ given above, to obtain a compound of formula 1, or (b) converting an amine of formula 6 into a compound of formula 1 by reductive amination with a suitable carbonyl compound in the presence of a reducing agent.

18. The method according to claim 17, wherein the compound of formula 6 is made by:

(a) taking up a compound of formula 2

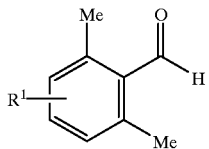

wherein R¹ has the meaning given in the respective claims 1 to 9, in trimethylsilylcyanide in a in the presence of a Lewis acid;

(b) diluting the resulting mixture using a suitable anhydrous organic solvent;

(c) reducing the diluted compound by means of a suitable reducing agent to form a compound of formula 3

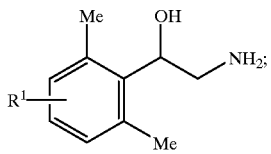

(d) reacting the product of the previous step with trifluoroacetic acid anhydride, optionally after separation of the enantiomers, by taking up in a suitable organic solvent in the presence of a suitable organic or inorganic base, to form a compound of formula 4

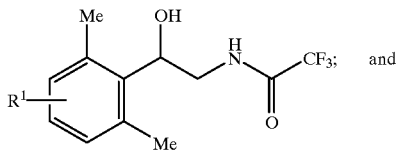

(e) dissolving the product of the previous step in a suitable organic solvent and reacting it in the presence of a suitable organic base with a compound of formula 5

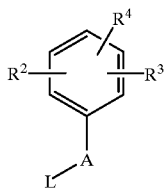

optionally dissolved in a suitable organic solvent, wherein the groups R², R³, and R⁴ have the meanings given in the respective claims 1 to 9, to form a compound of formula 6.

19. The method according to claim 17, wherein the compound of formula 6 is obtained by reacting a compound of formula 2

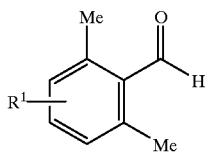

wherein R¹ has the meaning given in the respective claims 1 to 9, in a first step, using nitromethane in glacial acetic acid at elevated temperature, to obtain a compound of formula 7

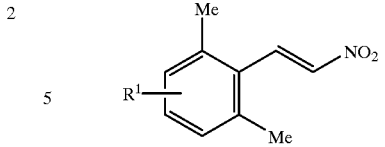

which is reacted in a suitable organic solvent by means of an alcohol 8

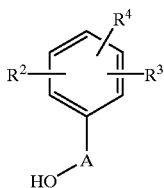

wherein the groups R², R³, and R⁴ have the meanings given in the respective claims 1 to 9, in the presence of a suitable base, to obtain an ether of formula 9

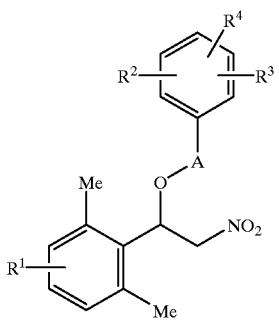

from which the compound of formula 6 may be obtained reductively, preferably by metal-catalyzed reduction.

20. A method for preparing compounds of formula 1 according to one of claims 1 to 9

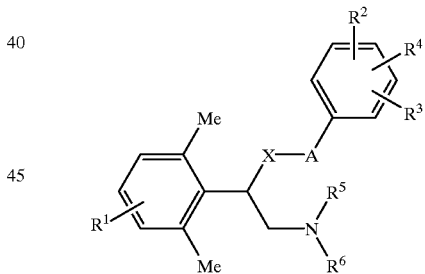

wherein the groups A, R¹, R², R³, R⁴, R⁵, and R⁶ have the meanings given in the respective claims 1 to 9 and wherein X is —NH—, the method comprising:

(a) reacting a compound of formula 3

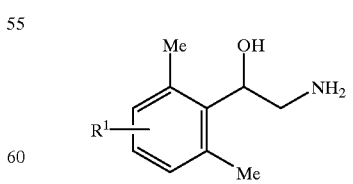

wherein the group R¹ has the meaning given in the respective claim 1 to 9, in a suitable organic solvent in the presence of a suitable inorganic or organic base using a suitable alkylating agent wherein the alkyl group has the definitions given in the respective claims 1 to 9 for R⁵ and R¹, to obtain a compound of formula 16

16

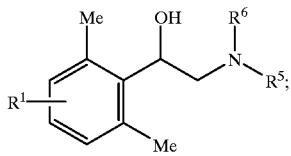

(b) reacting the product of the previous step, if $R^5$ or $R^6$ is hydrogen, using suitable protecting groups, by means of suitable halogenating reagents, suitable sulfonic acid chlorides, or suitable sulfonic acid anhydrides in the presence of suitable bases in suitable inert solvents to obtain a compound of formula 17

17

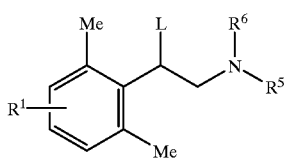

wherein L is a leaving group selected from chlorine, bromine, iodine, methanesulfonate, trifluoromethanesulfonate, and p-toluenesulfonate; and (c) reacting the product of the previous step in a suitable organic solvent in the presence of a suitable inorganic or organic base using a compound of formula 18

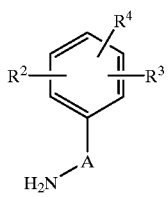

wherein the groups $R^2$, $R^3$, and $R^4$ have the meanings given in the respective claims 1 to 9, to obtain a compound of formula 1.

21. A process for preparing a compound of formula 1,

1

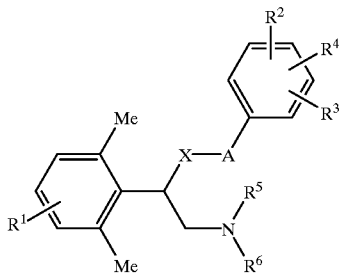

wherein the groups A, $R^1$, $R^2$, $R^3$, $R^4$, $R^5$, and $R^6$ have the meanings given in the respective claims 1 to 9 and wherein X denotes a group selected from —N(CHO)—, —N(CO—$C_1$–$C_6$-alkyl)-, —N($C_1$–$C_6$-alkyl)- and —N($C_3$–$C_6$-cycloalkyl-$C_1$–$C_4$-alkylene), the process comprising reacting a compound of formula 1 wherein X is —NH— is reacted in a suitable organic solvent in the presence of a suitable inorganic or organic base by means of a suitable alkylating, formylating, or acylating agent.

22. A pharmaceutical composition comprising an effective amount of a compound of formula 1 according to one of claims 1 to 8 and a conventional excipient or carrier.

23. A pharmaceutical composition comprising an effective amount of a compound of formula 1-Y according to one of claims 9 to 16 and a conventional excipient or carrier.

24. A method for treatment of functional disorders caused by overstimulation, in a host in need of such treatment or prophylaxis, which method comprises administering the host an effective amount of a compound of formula 1 according to one of claims 1 to 8.

25. A method for treatment of functional disorders caused by overstimulation, in a host in need of such treatment or prophylaxis, which method comprises administering the host an effective amount of a compound of formula 1-Y according to one of claims 9 to 16.

26. A method for treatment of arrhythmias, spasms, cardiac and cerebral ischemias, pain, and neurodegenerative disorders, in a host in need of such treatment or prophylaxis, which method comprises administering the host an effective amount of a compound of formula 1 according to one of claims 1 to 8.

27. A method for treatment of arrhythmias, spasms, cardiac and cerebral ischemias, pain, and neurodegenerative disorders, in a host in need of such treatment or prophylaxis, which method comprises administering the host an effective amount of a compound of formula 1-Y according to one of claims 9 to 16.

28. A method for treatment of epilepsy, hypoglycemia, hypoxia, anoxia, brain trauma, brain edema, cerebral stroke, perinatal asphyxia, degeneration of the cerebellum, amyotrophic lateral sclerosis, Huntington's disease, Alzheimer's disease, Parkinson's disease, cyclophrenia, hypotonia, cardiac infarct, heart rhythm disorders, angina pectoris, chronic pain, neuropathic pain and local anesthesia, in a host in need of such treatment or prophylaxis, which method comprises administering the host an effective amount of a compound of formula 1 according to one of claims 1 to 8.

29. A method for treatment of epilepsy, hypoglycemia, hypoxia, anoxia, brain trauma, brain edema, cerebral stroke, perinatal asphyxia, degeneration of the cerebellum, amyotrophic lateral sclerosis, Huntington's disease, Alzheimer's disease, Parkinson's disease, cyclophrenia, hypotonia, cardiac infarct, heart rhythm disorders, angina pectoris, chronic pain, neuropathic pain and local anesthesia, in a host in need of such treatment or prophylaxis, which method comprises administering the host an effective amount of a compound of formula 1-Y according to one of claims 9 to 16.

* * * * *